(12) United States Patent
Fallin et al.

(10) Patent No.: US 10,736,641 B2
(45) Date of Patent: Aug. 11, 2020

(54) OSTEOTOMY GUIDE AND METHOD

(71) Applicant: Smith & Nephew, Inc., Memphis, TN (US)

(72) Inventors: T. Wade Fallin, Hyde Park, UT (US); M. Mary Sinnott, Logan, UT (US)

(73) Assignee: Smith & Nephew, Inc., Memphis, TN (US)

( * ) Notice: Subject to any disclaimer, the term of this patent is extended or adjusted under 35 U.S.C. 154(b) by 130 days.

(21) Appl. No.: 15/886,029

(22) Filed: Feb. 1, 2018

(65) Prior Publication Data

US 2018/0153559 A1  Jun. 7, 2018

Related U.S. Application Data

(62) Division of application No. 13/527,359, filed on Jun. 19, 2012, now Pat. No. 9,907,558.

(60) Provisional application No. 61/568,137, filed on Dec. 7, 2011, provisional application No. 61/506,000, filed on Jul. 8, 2011, provisional application No. 61/506,004, filed on Jul. 8, 2011, provisional application No. 61/505,992, filed on Jul. 8, 2011.

(51) Int. Cl.
| | |
|---|---|
| *A61B 17/15* | (2006.01) |
| *A61B 17/88* | (2006.01) |
| *A61B 17/14* | (2006.01) |
| *A61B 90/00* | (2016.01) |
| *A61B 17/86* | (2006.01) |

(52) U.S. Cl.
CPC ........ *A61B 17/151* (2013.01); *A61B 17/8886* (2013.01); *A61B 17/142* (2016.11); *A61B 17/152* (2013.01); *A61B 17/86* (2013.01); *A61B 2090/037* (2016.02)

(58) Field of Classification Search
CPC ....... A61B 17/15–17/158; A61B 17/66; A61B 17/7216; A61B 17/7225; A61B 17/8004–17/8019; A61B 17/8866; A61B 2017/564; A61B 2017/565; A61B 2017/681
USPC .................................................. 606/87, 105
See application file for complete search history.

(56) References Cited

U.S. PATENT DOCUMENTS

| | | |
|---|---|---|
| 2,247,499 A | 7/1941 | Hutchison, Jr. |
| 2,345,881 A | 4/1944 | Nyquist |
| 3,900,025 A | 8/1975 | Barnes, Jr. |
| 4,069,824 A | 1/1978 | Weinstock |
| 4,622,960 A | 11/1986 | Tam |
| 4,627,425 A | 12/1986 | Reese |
| 4,664,102 A | 5/1987 | Comparetto |

(Continued)

FOREIGN PATENT DOCUMENTS

| | | |
|---|---|---|
| EP | 570187 A1 | 11/1993 |
| EP | 1452145 A1 | 9/2004 |

(Continued)

OTHER PUBLICATIONS

Australian Patent Examination Report; Australian Patent Office; Australian Patent Application No. 2012282919; dated Apr. 14, 2016; 3 pages.

(Continued)

*Primary Examiner* — Amy R Sipp

(57) ABSTRACT

A guide and method useful in cutting and rejoining bones is presented. The guide is particularly useful in performing an osteotomy of a long bone adjacent a joint such as a hand or foot.

19 Claims, 19 Drawing Sheets

(56) References Cited

U.S. PATENT DOCUMENTS

| | | |
|---|---|---|
| 4,708,133 A | 11/1987 | Comparetto |
| 4,750,481 A | 6/1988 | Reese |
| 4,838,254 A | 6/1989 | Gauthier |
| 4,929,247 A | 5/1990 | Rayhack |
| 4,952,214 A | 8/1990 | Comparetto |
| 5,035,698 A | 7/1991 | Comparetto |
| 5,042,983 A | 8/1991 | Rayhack |
| 5,059,201 A | 10/1991 | Asnis |
| 5,112,334 A | 5/1992 | Alchermes et al. |
| 5,147,364 A | 9/1992 | Comparetto |
| 5,176,685 A | 1/1993 | Rayhack |
| 5,413,579 A | 5/1995 | Du Toit |
| 5,470,335 A | 11/1995 | Du Toit |
| 5,529,075 A | 6/1996 | Clark |
| 5,569,257 A | 10/1996 | Amegger et al. |
| 5,601,565 A | 2/1997 | Huebner |
| 5,810,822 A | 9/1998 | Mortier |
| 5,843,085 A | 12/1998 | Graser |
| 5,925,049 A | 7/1999 | Gustilo et al. |
| 5,984,931 A | 11/1999 | Greenfield |
| 6,001,101 A | 12/1999 | Augagneur et al. |
| 6,007,535 A | 12/1999 | Rayhack et al. |
| 6,030,391 A | 2/2000 | Brainard et al. |
| 6,203,545 B1 | 3/2001 | Stoffella |
| 6,248,109 B1 | 6/2001 | Stoffella |
| 6,391,031 B1 | 5/2002 | Toomey |
| 6,676,662 B1 | 1/2004 | Bagga et al. |
| 6,689,136 B2 | 2/2004 | Stoffella |
| 7,572,258 B2 | 8/2009 | Stiernborg |
| 7,763,026 B2 | 7/2010 | Egger et al. |
| 8,246,661 B2 | 8/2012 | Beutter et al. |
| 8,777,948 B2 | 7/2014 | Bernsteiner |
| 2002/0165552 A1 | 11/2002 | Duffner |
| 2003/0045881 A1 | 3/2003 | Barouk et al. |
| 2003/0078599 A1 | 4/2003 | O'Quinn et al. |
| 2003/0078600 A1 | 4/2003 | O'Quinn et al. |
| 2003/0216742 A1 | 11/2003 | Wetzler et al. |
| 2004/0015177 A1 | 1/2004 | Chu |
| 2004/0210234 A1 | 10/2004 | Coillard-Lavirotte et al. |
| 2004/0236424 A1 | 11/2004 | Berez et al. |
| 2004/0260301 A1 | 12/2004 | Lionberger et al. |
| 2005/0033302 A1 | 2/2005 | Frank |
| 2006/0015102 A1 | 1/2006 | Toullec et al. |
| 2006/0058796 A1 | 3/2006 | Hartdegen et al. |
| 2006/0241607 A1 | 10/2006 | Myerson et al. |
| 2006/0264961 A1 | 11/2006 | Murray-Brown |
| 2007/0010818 A1 | 1/2007 | Stone et al. |
| 2007/0083362 A1 | 4/2007 | Moriya et al. |
| 2007/0233128 A1 | 10/2007 | Schmieding et al. |
| 2007/0265634 A1 | 11/2007 | Weinstein |
| 2007/0270850 A1 | 11/2007 | Geissler |
| 2009/0036931 A1 | 2/2009 | Pech et al. |
| 2009/0177208 A1 | 7/2009 | Strnad et al. |
| 2009/0254126 A1 | 10/2009 | Orbay et al. |
| 2010/0036430 A1 | 2/2010 | Hartdegen et al. |
| 2010/0057216 A1 | 3/2010 | Gannoe et al. |
| 2010/0256687 A1 | 10/2010 | Neufeld et al. |
| 2010/0324563 A1 | 12/2010 | Green, II et al. |
| 2011/0004254 A1 | 1/2011 | Beger et al. |
| 2011/0066165 A1 | 3/2011 | Skinlo et al. |
| 2011/0144647 A1 | 6/2011 | Appenzeller et al. |
| 2011/0178524 A1 | 7/2011 | Lawrence et al. |
| 2011/0238068 A1* | 9/2011 | Bernsteiner ............ A61B 17/15 606/70 |

FOREIGN PATENT DOCUMENTS

| | | |
|---|---|---|
| EP | 1952776 A1 | 8/2008 |
| EP | 1707142 B1 | 3/2010 |
| GB | 2475491 A | 5/2011 |
| WO | 2000006036 A1 | 2/2000 |
| WO | 2003075775 A1 | 9/2003 |
| WO | 2004089227 A2 | 10/2004 |
| WO | 2005041785 A1 | 5/2005 |
| WO | 2008003433 A1 | 1/2008 |
| WO | 2008043380 A1 | 4/2008 |
| WO | 2008076559 A1 | 6/2008 |
| WO | 2008149308 A1 | 12/2008 |
| WO | 2010060124 A1 | 6/2010 |

OTHER PUBLICATIONS

Chinese First Office Action; Chinese Patent Office (State Intellectual Property Office, PR China); Chinese Patent Application No. 201280043613.2; dated Dec. 29, 2015; 10 pages.

Extended European Search Report; European Patent Office; European Application No. 12810809.9; dated Feb. 15, 2016; 21 pages.

International Search Report; International Searching Authority; International PCT Application No. PCT/US2012/045584; dated Jan. 31, 2013; 3 pages.

Written Opinion; International Searching Authority; International PCT Application No. PCT/US2012/045584; dated Jan. 31, 2013; 4 pages.

International Preliminary Report on Patentability; the International Bureau of WIPO; International PCT Application No. PCT/US2012/045584; dated Jan. 14, 2014; 5 pages.

Supplementary Partial European Search Report; European Patent Office; European Patent Application No. 12810809.9; dated Apr. 1, 2015; 6 pages.

2013 BIOPRO, "Bunion Osteotomy Guide"; http://www.bioproimplants.com/product/bunion; 4 pages.

Blitz et al.; "Plantar Plate Repair of the Second Metatarsophalangeal Joint: Technique and Tips"; Journal of Foot & Ankle Surgery; 2004 43(4):266-270.

Coughlin et al.; "Second MTP Joint Instability: Grading of the Deformity and Description of Surgical Repair of Capsular Insufficiency"; The Physician and Sportmedicine; Sep. 3, 2011; 39(3):132-141.

Fleming and Camasta; "Plantar Plate Dysfuction"; Chapter 4; 2002; pp. 22-28; http://www.podiatryinstitute.com/pdfs/Update_2002/2002_04.pdf.

Gregg et al.; "Plantar Plate Repair and Weil Osteotomy for Metatarsophalangeal Joint Instability"; Foot and Ankle Surgery; 2007; 13:116-121.

Nery et al.; "Lesser Metatarsophalangeal Joint Instability: Prospective Evaluation and Repair of Plantar Plate and Capsular Insufficiency"; Foot and Ankle International; Apr. 2012; vol. 33(4); 301-311.

Weil et al.; "Anatomic Plantar Plate Repair Using the Weil Metatarsal Osteotomy Approach"; Foot and Ankle Specialist; Jun. 22, 2011; 4:145-150; originally published online on Mar. 18, 2011; http://fas.sagepub.com/content/4/3/145.

\* cited by examiner

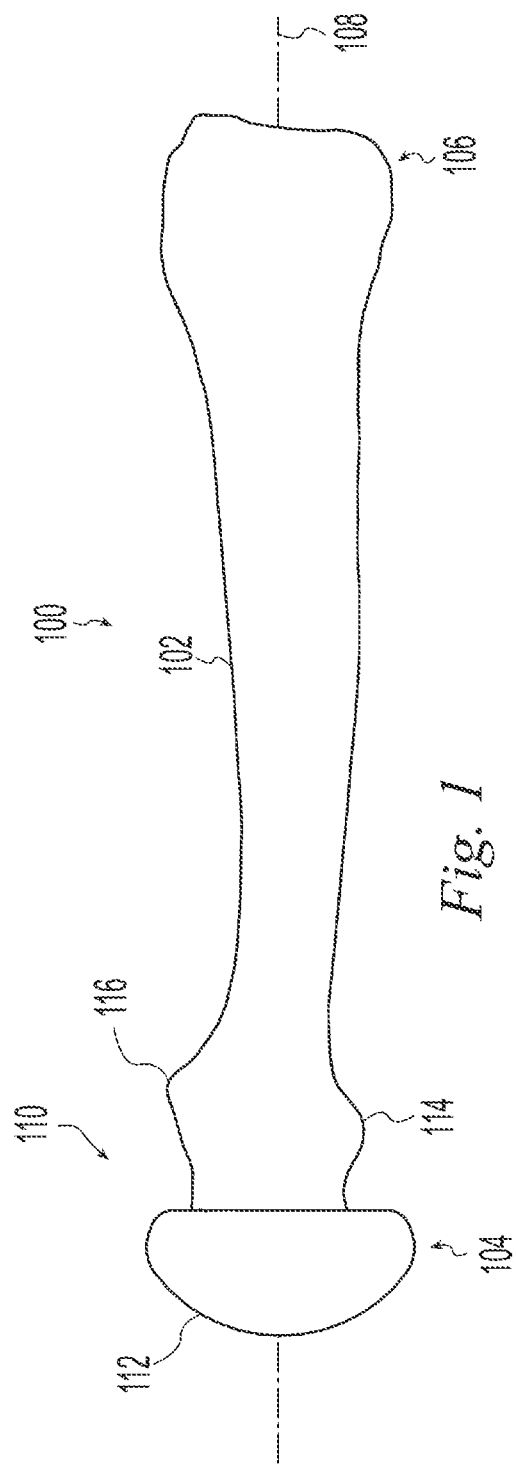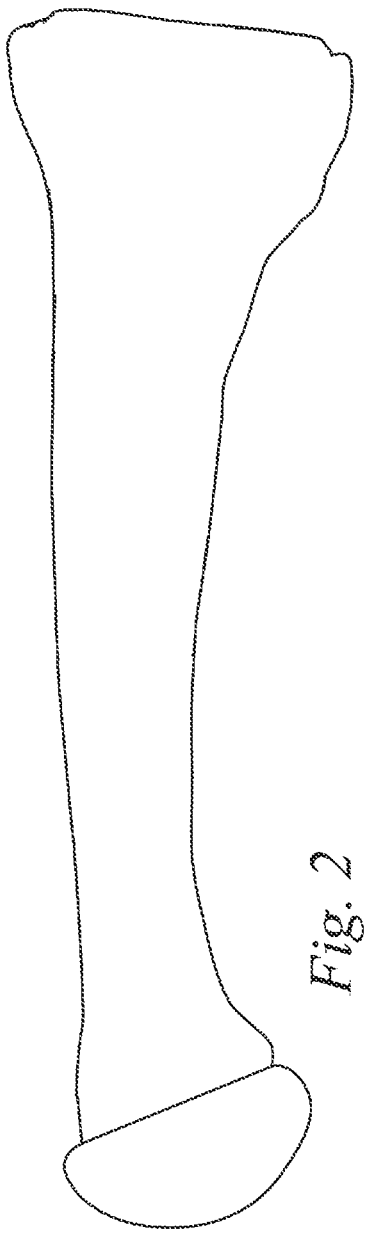

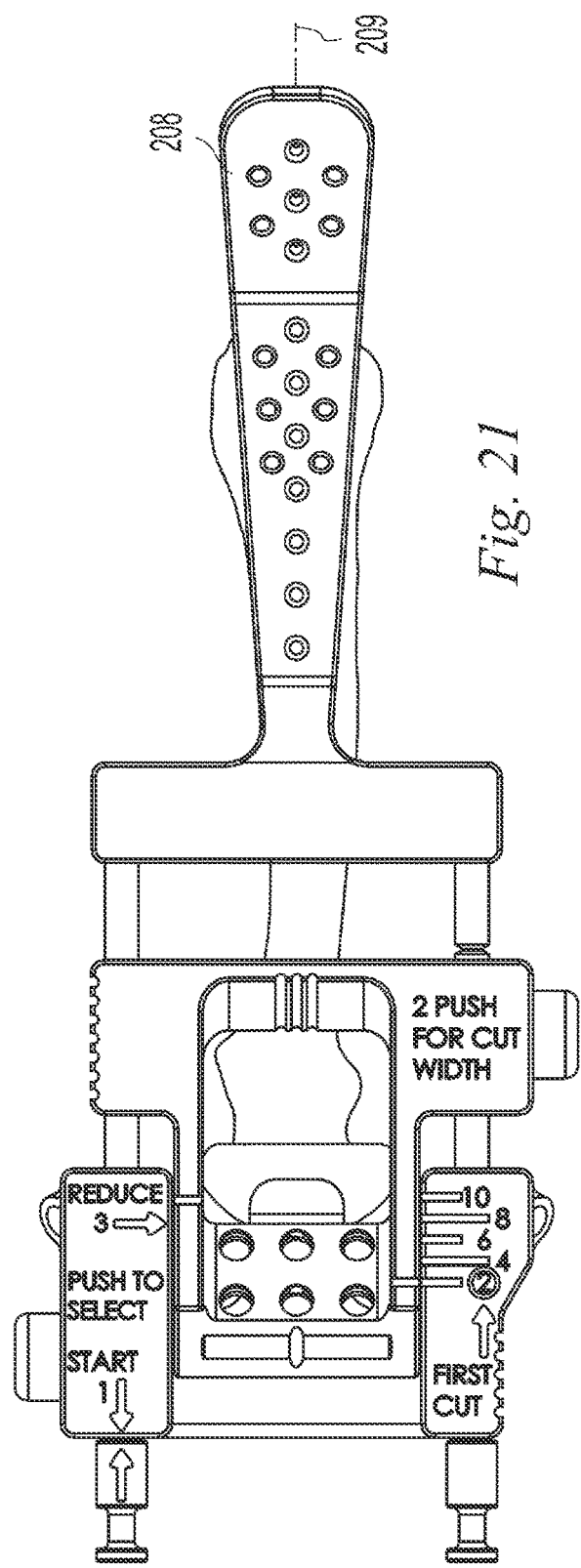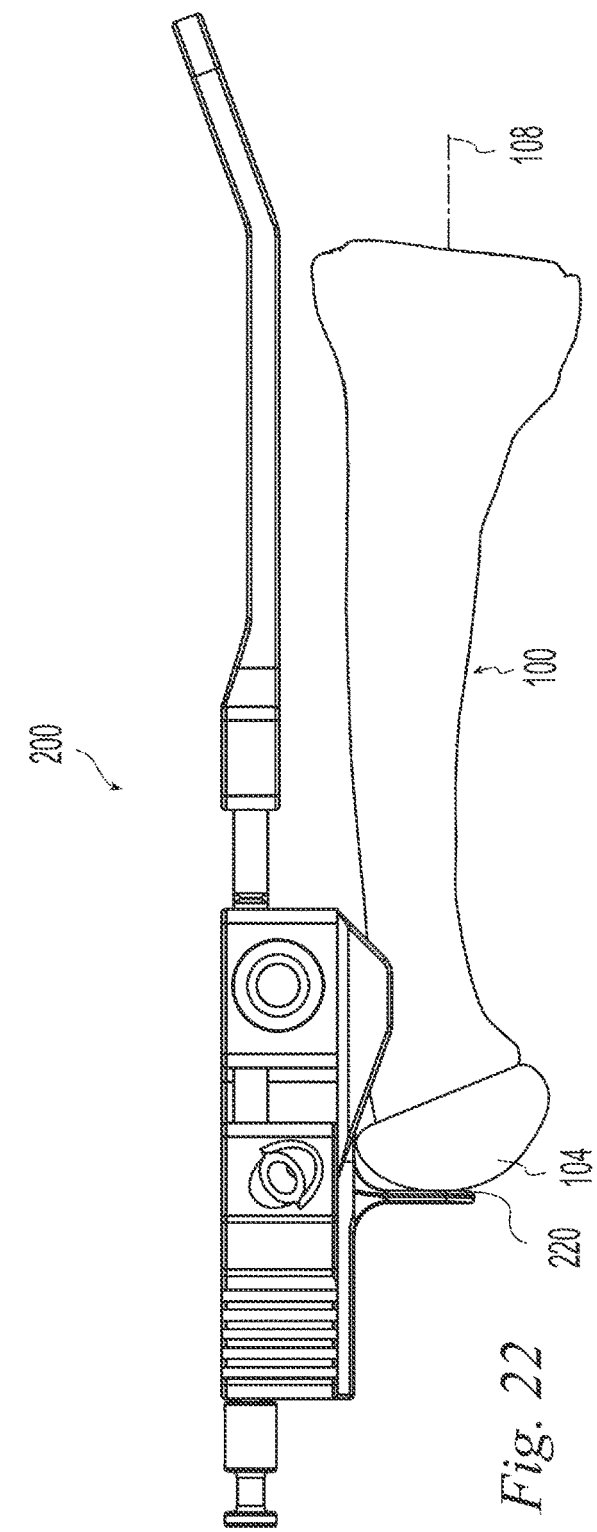

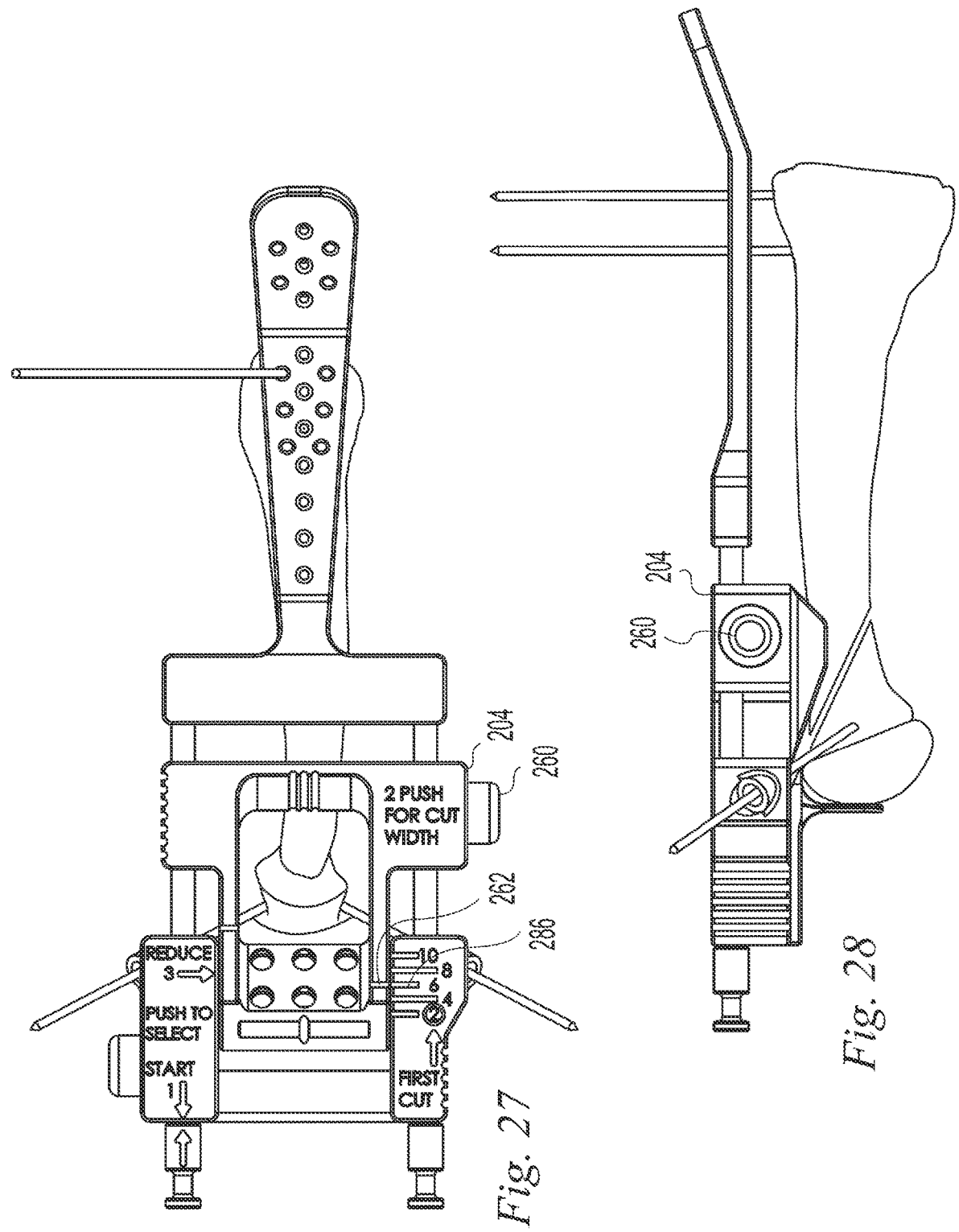

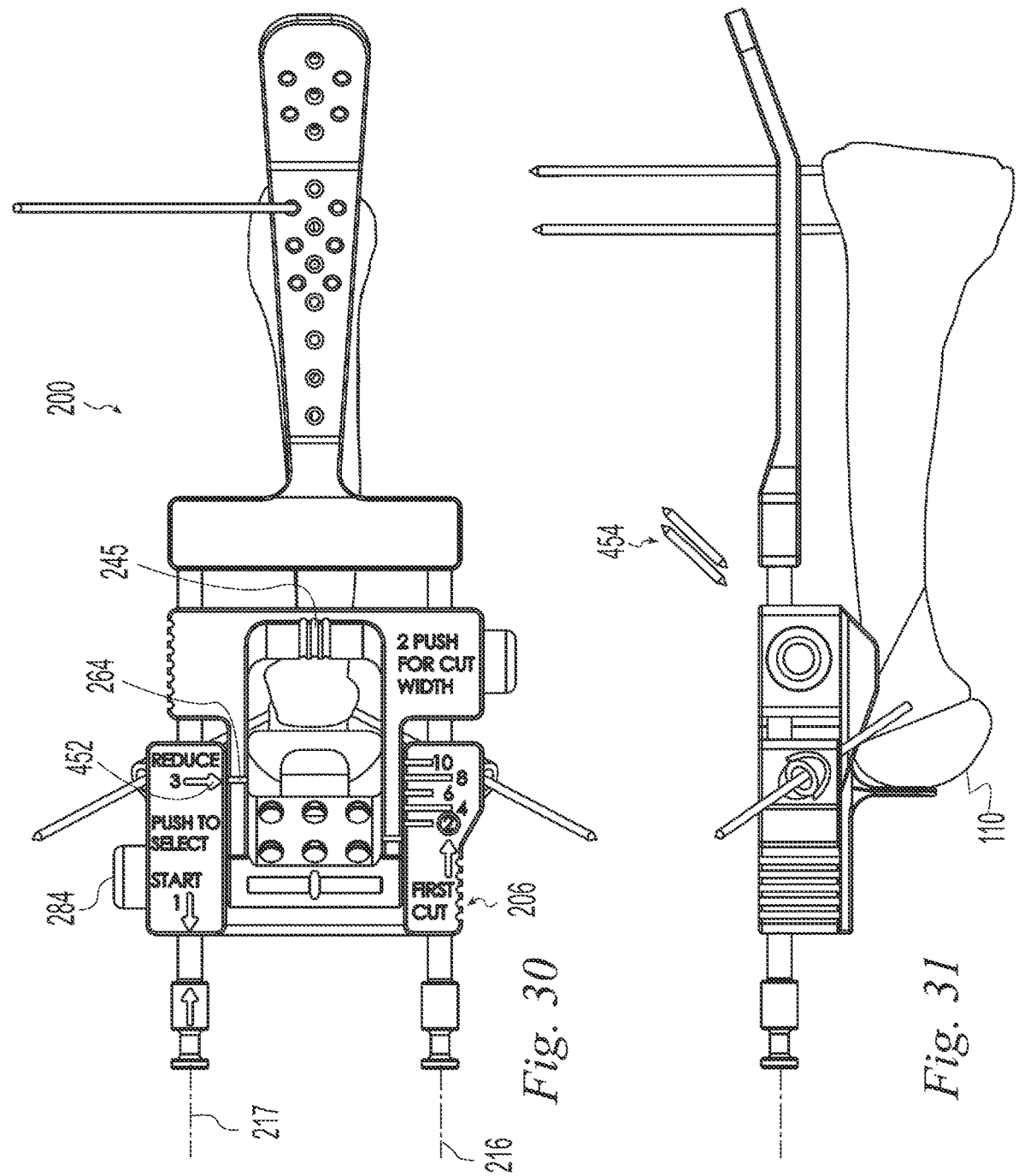

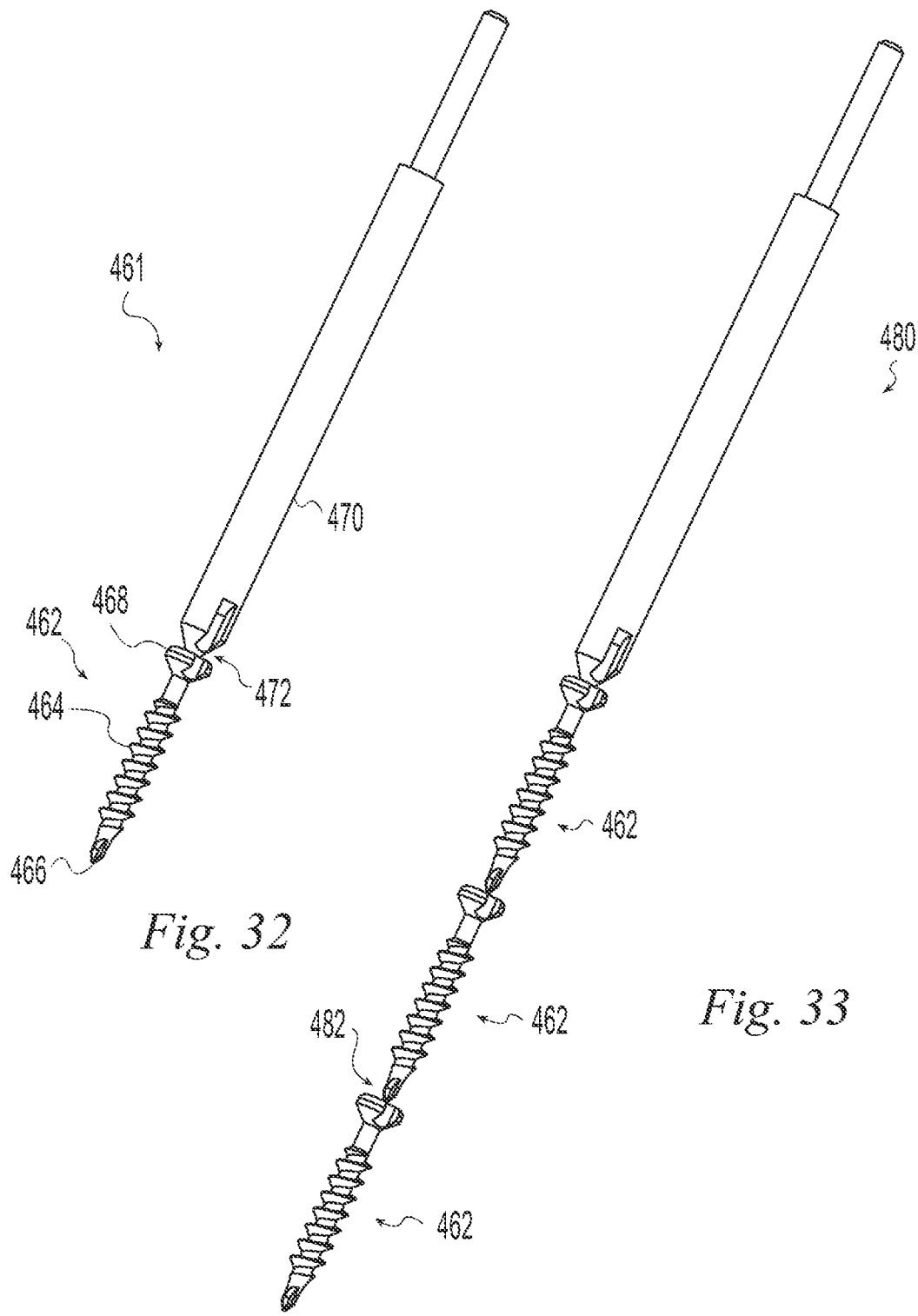

OSTEOTOMY GUIDE AND METHOD

CROSS-REFERENCE TO RELATED APPLICATIONS

This application is a divisional of U.S. patent application Ser. No. 13/527,359, filed Jun. 19, 2012, which claims the benefit of U.S. Provisional Application No. 61/568,137, filed Dec. 7, 2011, U.S. Provisional Application No. 61/505,992, filed Jul. 8, 2011, U.S. Provisional Application No. 61/506,000, filed Jul. 8, 2011, and U.S. Provisional Application No. 61/506,004, filed Jul. 8, 2011, the contents of each applicatiion hereby incorporated by reference in their entireties.

FIELD OF THE INVENTION

The invention relates to devices and methods suitable for performing surgery and in particular for performing an osteotomy in bones adjacent a joint such as for example of the foot or hand.

BACKGROUND

Various conditions may affect skeletal joints such as the elongation or rupture of soft tissues, shortening or contracture of soft tissues, malformation of bones, and a variety of other conditions associated with the joint. Surgical intervention may be facilitated by cutting bones adjacent a joint. For example, in order to correct the length of a bone, correct the orientation of the bone, or provide room to access soft tissues surrounding the bone, an osteotomy may be performed by cutting the bone to form two relatively moveable bone portions and then rejoining the portions.

Prior techniques for performing osteotomies have included freehand cutting of the bone followed by reducing the bone fragments by sliding one bone fragment relative to the other along the cut bone surface. Such a technique changes the biomechanics of the bone. For example, adjacent a joint, such a technique changes the instantaneous axis of rotation of the joint and the direction of pull of tendons acting on the joint resulting in non-anatomic joint function.

SUMMARY

The present invention provides a guide and method for performing an osteotomy

In one aspect of the invention, a guide provides a stable base with a cutter guide operable to guide a cutter to separate the bone into two, relatively moveable portions.

In another aspect of the invention, a guide includes a cutter guide operable to guide a cutter to form two parallel cuts transverse to the bone axis to remove a predetermined portion of the bone.

In another aspect of the invention, a guide provides a reduction mechanism operable to reduce a gap between two bone portions with motion along a predefined path. For example, a guide may be provided with a mechanism to reduce an osteotomy along the axis of the bone. This advantageously preserves joint mechanics of a joint including the cut bone by maintaining the instantaneous axis of rotation in the same position relative to the bone axis. In another example, a guide may be provided with a mechanism to move portions of a bone linearly at an angle transverse to the bone axis. In another example a guide may be provided with a mechanism to move portions of a bone along a non-linear path.

In another aspect of the invention, a guide may include references such as one or more reference surfaces, edges, axes, or points that engage or are alignable relative to one or more anatomical landmarks of the bone to position a cutter guide and/or a reduction mechanism in a predetermined relationship relative to the bone. For example, the cutter guide may be oriented relative to the one or more reference surfaces to guide a cutter to cut the bone so that the cut surfaces are oriented relative to the dominate loads on the bone to promote healing. For example, the cutter guide may cut the bones so that the cut bone surfaces are normal to the typical load on the bone to reduce shear forces that may interfere with healing of the osteotomy. In another example, the reduction mechanism may be oriented relative to the one or more reference surfaces to guide reduction of the bone portions along a mechanical axis of the bone so that the healed osteotomy will result in the same kinematic relationships within an associated joint.

In another aspect of the invention, a guide may include a fixation mechanism to attach the guide to the bone in a predetermined relationship. The guide may include a cutter guide portion operable to guide a cutter to separate the bone into two relatively moveable portions and the fixation mechanism may capture the two bone portions so that their relative positions are maintained according to a predetermined relationship. The guide may include a reduction mechanism operable to guide the two bone portions along a predefined axis as they are brought together to be joined. For example, the guide may include a first stage and a second stage joined together in linear translating relationship along a single translational degree of freedom. The stages may be fixed to a bone. The guide may guide a cutter to separate the bone into two relatively moveable portions with one portion being attached to each of the first and second stages. The stages may then be operable to move along the single translational degree of freedom to move the bone portions together so that the cut surfaces of the bone portions abut one another. One or more fasteners may then be used to attach the bone portions to one another.

In another aspect of the invention, a guide includes a base member, a first stage mounted to the base member in relative translating relationship, and a second stage mounted to the base member in relative translating relationship independent of the first stage. The base member may include a fixation mechanism operable to attach the base member to a first portion of an underlying bone. The second stage may include a fixation mechanism operable to attach the second stage to a second portion of the underlying bone. The first stage may include a cutter guide operable to guide a cutter to cut the bone. The first stage may be moved between different translated positions to guide the cutter to make spaced apart parallel cuts into the bone to remove a predetermined amount of bone between the first and second portions of the bone with parallel cut surfaces. The second stage may then be translated relative to the base to move the second portion of bone into contact with the first portion of bone.

In another aspect of the invention, the guide may include a fastener guiding portion operable to guide placement of the one or more fasteners in a predetermined orientation relative to the cut surfaces of the bone. For example, a fastener guide may be operable to place the one or more fasteners normal to the cut surfaces.

In another aspect of the invention, a guide may be configured to cut a metatarsal bone of a metatarsophalangeal joint of the human foot. The guide may include a planar reference surface engageable with the articular surface of the metatarsus to eliminate one translational degree of freedom. The guide may include a second planar reference surface engageable with the dorsal aspect of the metatarsal head or another portion of the dorsal surface of the metatarsus to eliminate another translational degree of freedom. The guide may include a center plane alignable with the axis of the metatarsus to eliminate a third translational degree of freedom and one rotational degree of freedom. Positioning the second planar surface parallel to the transverse body plane or the dorsal surface of the foot eliminates the remaining two rotational degrees of freedom. The guide may include first and second stages mounted to a base member in translating relationship along a reduction axis constraining the stages to a single translational degree of freedom. The base member and second stage may each receive one or more fasteners operable to join each in fixed relationship to an underlying portion of the metatarsus. For example, the base and second stage may each have at least two angled holes operable to receive pins that are driven into the bone. The angled pins constrain each portion of the metatarsus in six degrees of freedom relative to the base and second stage. A cutter guide mounted to the first stage may be operable to guide a cutter to cut the metatarsus parallel to the plantar surface of the foot when the patient is standing to promote healing of the osteotomy. The first stage may be repositionable relative to the underlying bone to guide multiple parallel cuts to remove a predetermined amount of bone. The second stage may then be moved relative to the base member to reduce the osteotomy along the mechanical axis of the metatarsus. When the bones abut, a fastener guide may be used to guide a fastener into the bone to fix the bone portions together. The constrained reduction maintains the relationship of the metatarsal head relative to the mechanical axis of the metatarsus to preserve the joint kinematics.

A fixation mechanism may include one or more pins, screws, straps, and other suitable fixation mechanisms.

Guide reference surfaces may be flat, convex, concave, cylindrical, spherical, or any other suitable shape to engage or align relative to a landmark.

Anatomic landmarks may include one or more articular joint surfaces, bone axes, intramedullary canals, joint planes, body planes, bone shafts, condyles, epicondyles, ligament attachments, or any other suitable landmark.

A cutter guide portion may include one or more planar surfaces, notches, grooves, holes, tubes, slots or other guiding portion able to guide a cutter in predetermined known relationship to the guide.

A cutter may include an oscillating saw, a reciprocating saw, a rotary saw, a band saw, an end mill, an osteotome, a water jet, or any other suitable cutter.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 1 is a dorsal view of the metatarsus of the right second metatarsophalangeal joint of the human foot;

FIG. 2 is a medial view of the bone of FIG. 1;

FIG. 21 is a top plan view of the guide of FIG. 3 showing a position of the guide on a metatarsus;

FIG. 22 is a side elevation view of the guide of FIG. 3 showing the position of FIG. 21;

FIG. 27 is a top plan view of the guide of FIG. 3 showing a position of the guide on a metatarsus;

FIG. 28 is a side elevation view of the guide of FIG. 3 showing the position of FIG. 27;

FIG. 30 is a top plan view of the guide of FIG. 3 showing the guide in use to reduce an osteotomy on a metatarsus;

FIG. 31 is a side elevation view of the guide of FIG. 3 showing the position of FIG. 30 and a pins being inserted to secure the osteotomy;

FIG. 32 is a perspective view of an osteotomy fixation screw according to the present invention;

FIG. 33 is a perspective view of an osteotomy fixation screw according to the present invention.

DESCRIPTION OF THE ILLUSTRATIVE EXAMPLES

Figure 3:
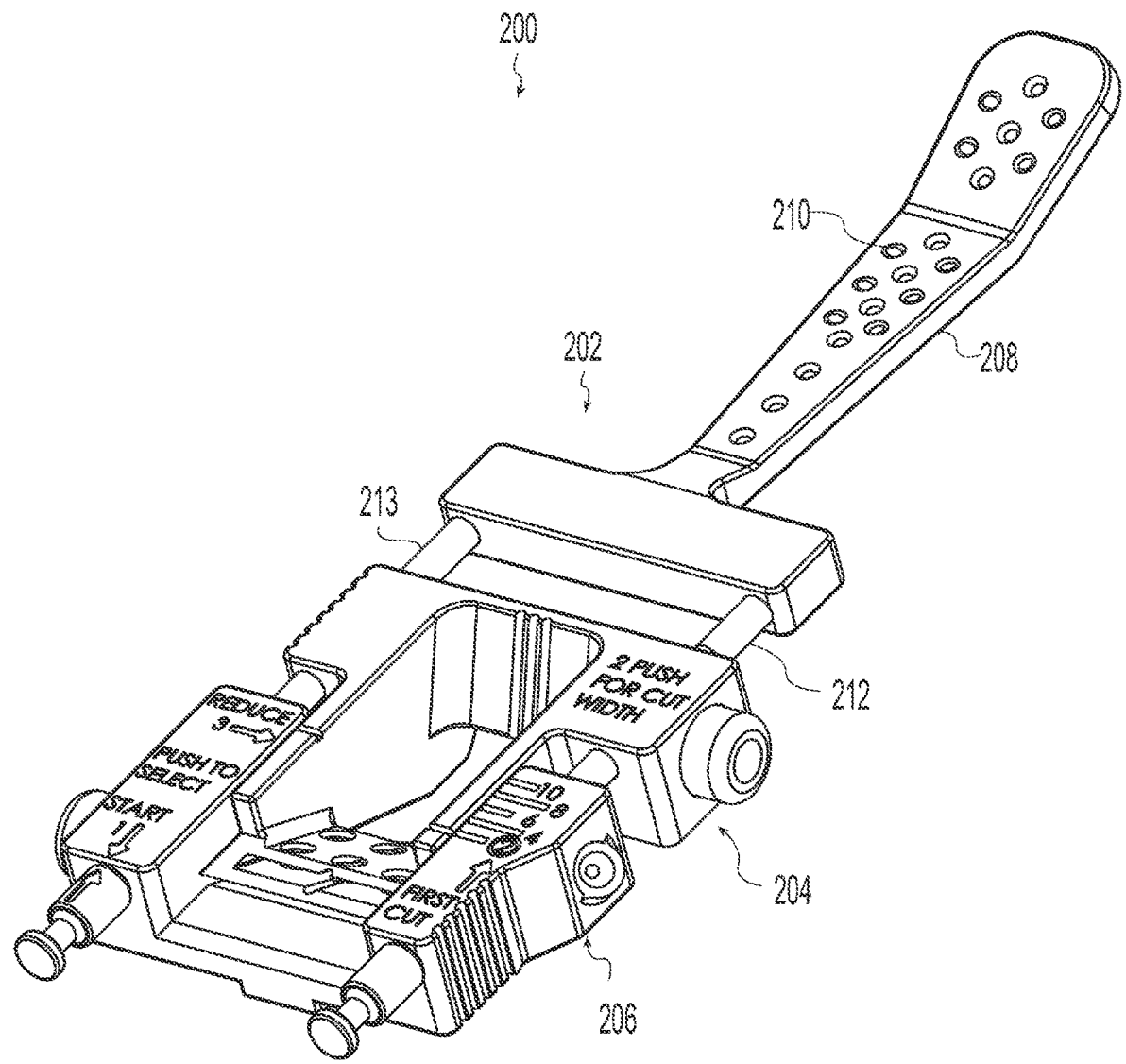
FIG. 3 is a perspective view of an illustrative example of a guide according to the present invention.
Figure 4:
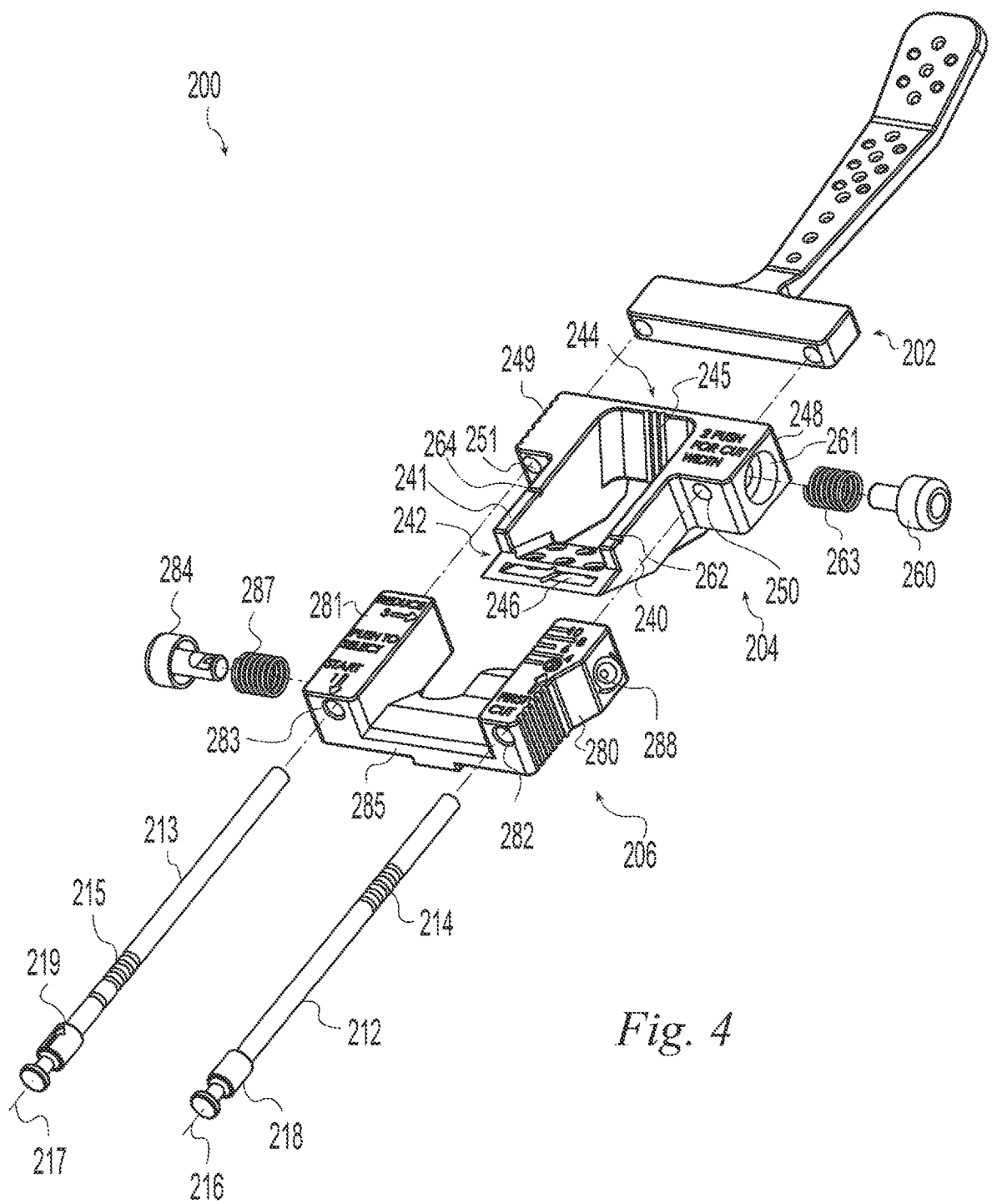
FIG. 4 is an exploded perspective view of the guide of FIG. 3.
Figure 5:
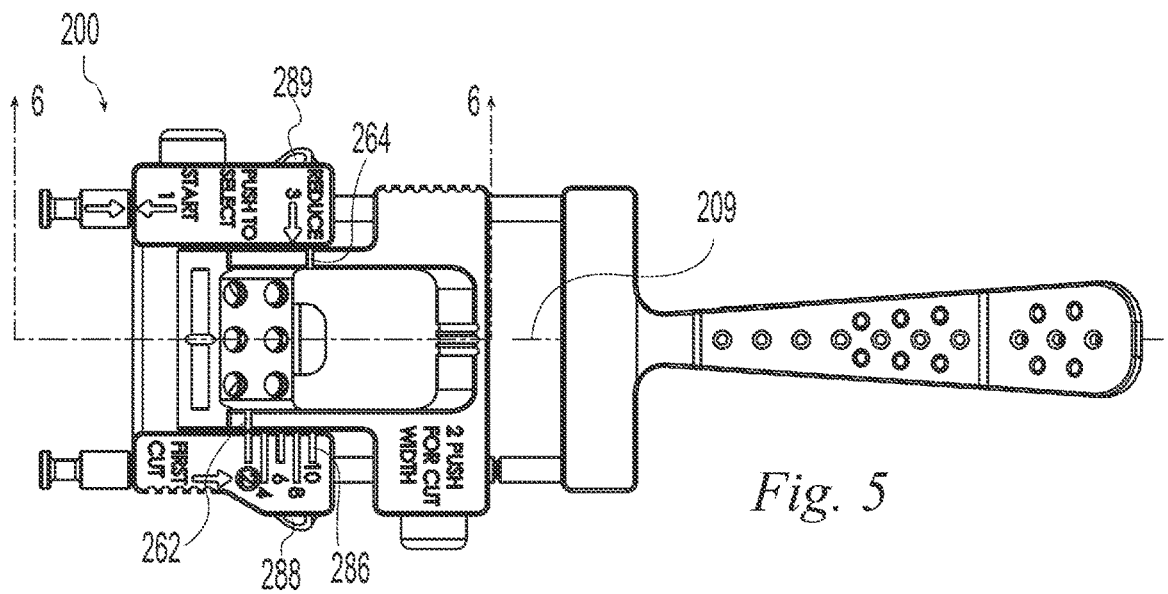
FIG. 5 is a top plan view of the guide of FIG. 3.

The following illustrative examples illustrate instruments and techniques for treating bones. Instruments and techniques according to the present invention may be used in conjunction with any bone but the illustrative examples are shown in a size and form most suitable for the joints of the hand and foot. In particular, the illustrative examples depict their use on a metatarsal bone adjacent the second metatarsophalangeal (MTP) joint of the human foot. The illustrative instruments and techniques are also suitable for use on metacarpal bones of the human hand. The term transverse is used herein to mean crossing as in non-parallel.

FIGS. 1 and 2 illustrate a bone 100 on which an osteotomy may be performed. In the descriptions that follow, t he bone 100 will be referred to as the metatarsus 100, and more particularly as the metatarsus 100 of the second MTP joint of the right foot. However, as noted above, the bone 100 may instead be another bone, such as a metacarpal bone. The metatarsus 100 includes an elongated shaft 102, a first or distal end 104, a second or proximal end 106, and a mechanical axis 108 extending from the first end 104 to the second end 106. The first end defines a head 110 having an articular surface 112 of the second MTP joint. A medial epicondyle 114 and a lateral epicondyle 116 each protrude outwardly from the shaft 102 proximal the head 110.

FIGS. 3-11 depict an illustrative example of an osteotomy guide 200 and technique for use, e.g., in relatively repositioning first and second portions of a bone. For example, the guide 200 may be used to shorten a metatarsal bone by moving proximal and distal portions of the bone closer together. The illustrative osteotomy guide 200 provides a stable base with a cutter guide operable to guide a cutter to separate the bone into two, relatively moveable portions. The cutter guide is further operable to guide a cutter to form two parallel cuts transverse to the bone axis to remove a predetermined portion of the bone. The illustrative osteotomy guide 200 provides a reduction mechanism operable to reduce a gap between the two bone portions with motion along a predefined axis.

The guide 200 includes a proximal base member 202, an intermediate inner stage 204, and a distal outer stage 206 all mounted in relative translating relationship. The base member 202 includes an elongated plate-like handle 208 including a plurality of fixation holes 210. First and second spaced apart, parallel guide arms 212, 213 are rigidly joined to the base member and extend opposite the elongated handle 208.

The arms include annular notches 214, 215 for controlled positioning of the stages at discrete locations along the arms. The arms define parallel translation axes 216, 217. Each arm has a radially enlarged stop 218, 219 near its distal end against which the outer stage 206 may abut to define a distal limit of travel of the outer stage 206 on the arms 212, 213.

The inner stage 204 is a generally box-like member having first and second opposed sides 240, 241 joined at one end by a first end wall defining a cutter guide 242 and at an opposite end by a second end wall 244. The second end wall 244 includes fixation guide grooves 245 formed in a plane transverse to the translation axes 216, 217. In the illustrative example of FIGS. 3-11, the cutter guide 242 is in the form of a saw guide having a saw blade guiding slot 246. The sides 240, 241 include outwardly extending bosses 248, 249 having through holes 250, 251 for receiving the guide arms 212, 213 in sliding engagement so that the inner stage 204 may be moved axially along the translation axes 216, 217.

The saw blade guiding slot 246 defines a plane oriented relative to the translation axes 216, 217 to guide a saw blade in a predetermined orientation relative to the axes 216, 217. In the illustrative example of FIGS. 3-11, the slot 246 forms an angle 252 (FIG. 6) relative to the plane defined by the axes 216, 217. This angle 252 is selected to minimize the shear stresses on the healing osteotomy. For example, in the illustrative example of FIGS. 3-11, the angle is chosen based on typical metatarsal anatomy. In a typical patient standing upright on a level floor, the metatarsal axis 108 forms an angle of approximately 10-40 degrees relative to the floor. It is desirable for the osteotomy cut surfaces to be parallel to the floor such that when the patient is standing upright there is little or no shear force in the plane of the healing bone surfaces. In use, the guide axes, 216, 217 are oriented parallel to the metatarsal axis 108. Therefore, the blade guiding slot 246 is preferably oriented at an angle 252 of 10-40 degrees relative to the guide axes 216, 217 to produce the desire cut. More preferably, the angle 252 is 15-30 degrees. In the illustrative example of FIGS. 3-11, the angle 252 is 25 degrees.

A button 260 is received in a hole 261 formed in the first side 240 and biased by a spring 263. The button 260 includes a feature engageable with the annular notches 214 of the first arm 212 to selectively lock the position of the inner stage 204 relative to the arm as will be explained more fully below. The feature may be, e.g., a ring, notch, pin, or other feature engageable with the annular notches 214. The first side 240 includes a reference mark 262 to indicate the position of the inner stage relative to the outer stage to indicate cut width as will be explained more fully below. The second side 241 includes a reference mark 264 to indicate the position of the inner stage relative to the outer stage to indicate bone reduction as will be explained more fully below.

Figure 6:
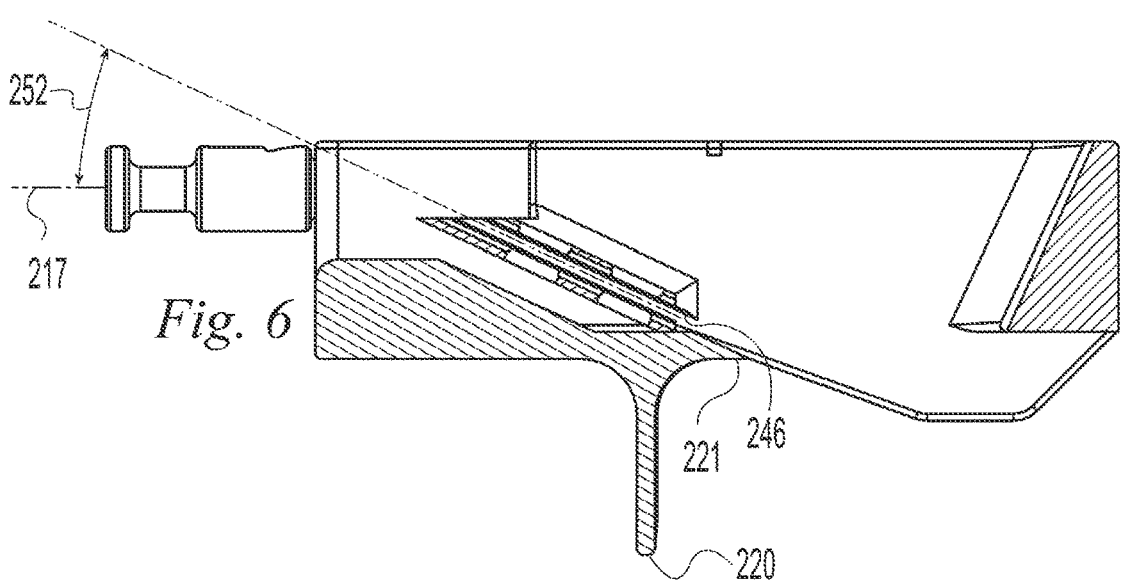
FIG. 6 is a side sectional view of the guide of FIG. 3 taken along line 6-6 of FIG. 5.
Figure 7:
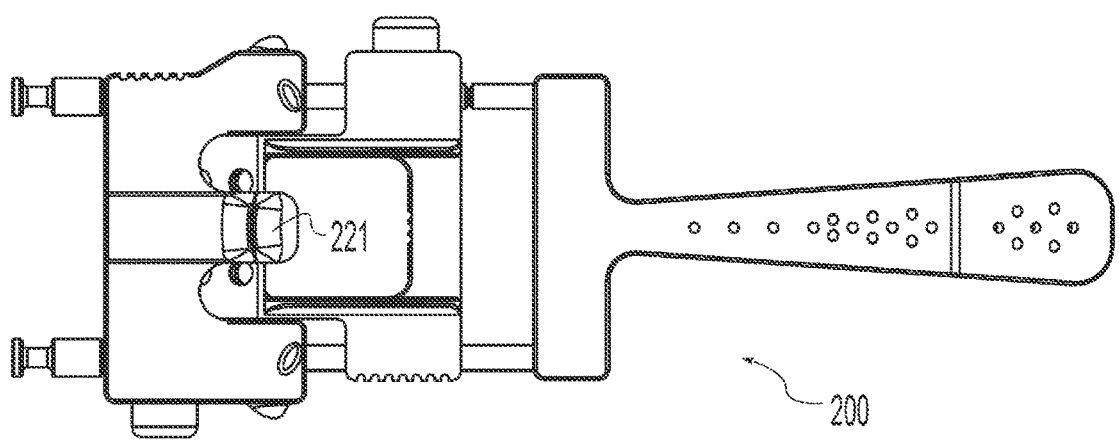
FIG. 7 is a bottom plan view of the guide of FIG. 3.
Figure 8:
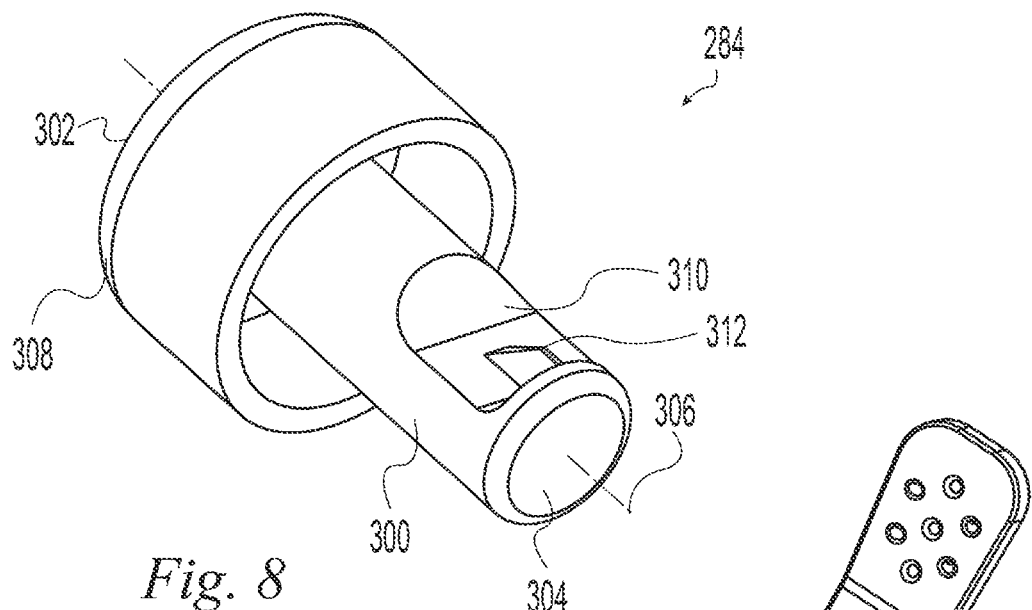
FIG. 8 is a perspective view of a component pushbutton of the guide of FIG. 3.
Figure 9:
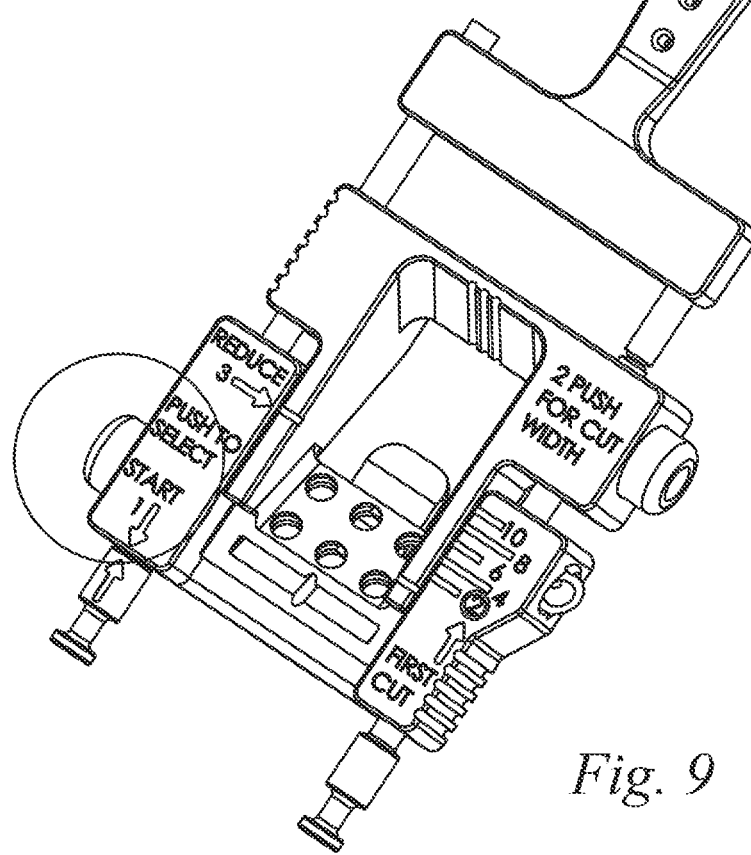
FIG. 9 is a perspective view of the guide of FIG. 3 highlighting a portion.

The outer stage 206 is a generally U-shaped member having first and second sides 280, 281 joined at a first end by a first end wall 285 and open at the second end. The outer stage 206 includes fixation holes 288, 289 for receiving fixation devices, e.g. pins, screws or the like, to attach the outer stage to the metatarsal bone near the head. The outer stage 206 further includes a first reference member 220 extending downwardly away from the stage as best seen in FIG. 6 and a second reference member 221 extending proximally between the first and second sides. The sides 280, 281 include through holes 282, 283 for receiving the guide arms 212, 213 in sliding engagement so that the outer stage 206 may be moved axially along the translation axes 216, 217. A button 284, similar to button 260, is received in a hole (not shown) in the second side 281 and is biased by a spring 287. The button 284 is engageable with the annular notches 215 to selectively lock the axial position of the outer stage relative to the arms. The first side 280 includes reference marks, or indicia 286, indicating the relative position of the inner stage relative to the outer stage. The indicia 286, reference mark 262, and annular notches 214, 215 are arranged so that the reference mark 262 aligns with indicia 286 to indicate the relative position of the inner stage, and thus the saw slot 246, relative to the outer stage.

Further detail of buttons 260 and 284 and their operation is illustrated in FIGS. 8-11 using button 284 as an example. The button 284 includes a shaft 300 extending from a first end 302 to a second end 304 along an axis 306. The first end 302 defines an enlarged head 308. The shaft includes a notch 310 transverse to the axis 306 and able to receive a portion of the second guide arm 215 in transverse sliding relationship. A key 312 projects into and blocks a portion of the notch 310. The button 284 and spring 287 are placed into the hole in the second side 281 of the outer stage 206. The second arm 213 is inserted through the hole 283 in the second side 281 of the outer stage 206 and through the notch 310 in the button shaft 300. The arm 213 abuts a portion of the button 284 and retains the button in the outer stage 206.

Figure 10:
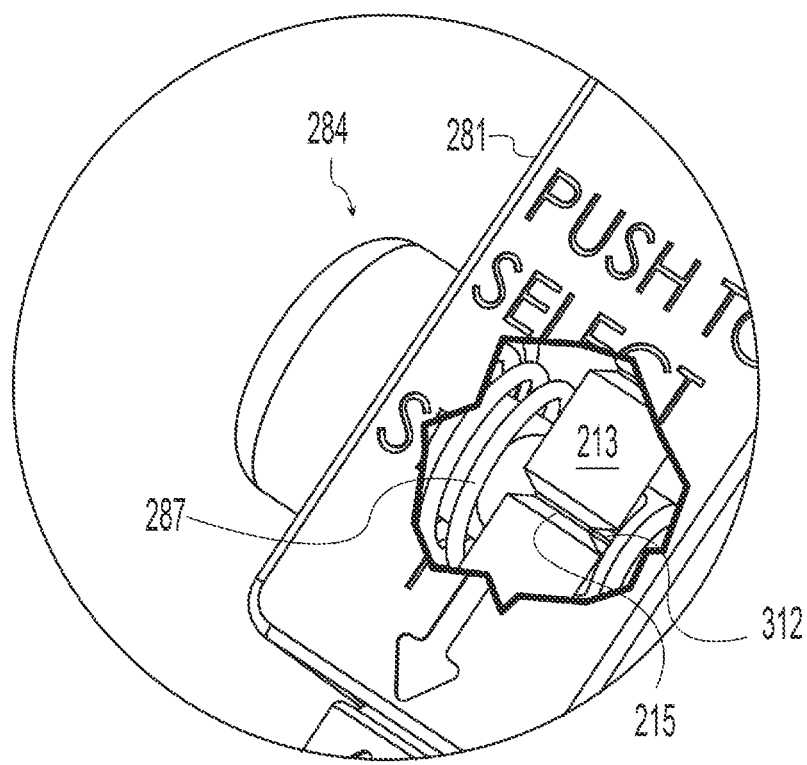
FIG. 10 is a cutaway perspective view of the guide of FIG. 3 detailing the portion highlighted in FIG. 9 showing the operation of the pushbutton of FIG. 8.
Figure 11:
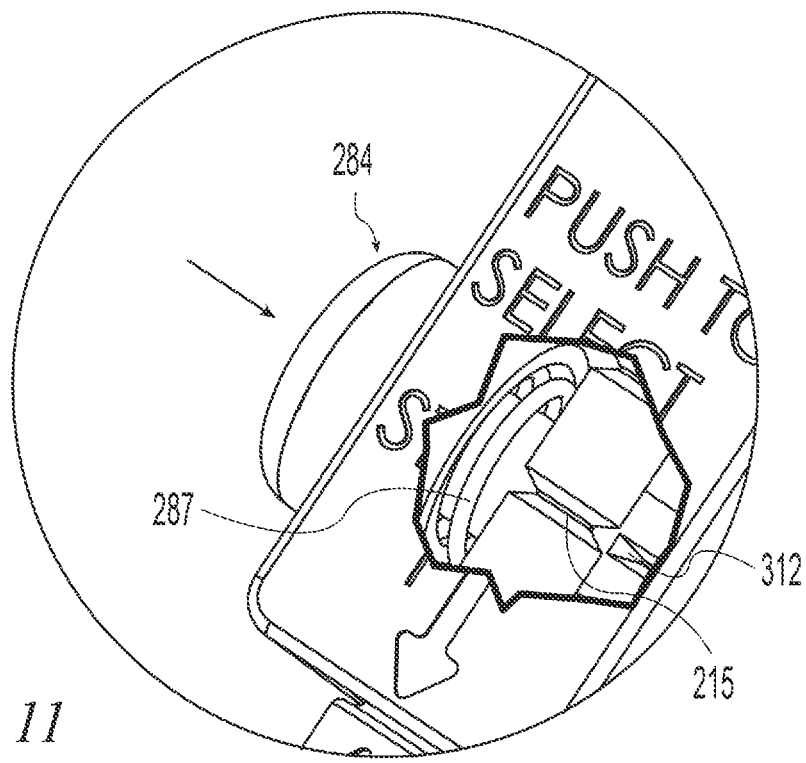
FIG. 11 is a cutaway perspective view of the guide of FIG. 3 detailing the portion highlighted in FIG. 9 showing the operation of the pushbutton of FIG. 8.

The spring 287 biases the button 284 outwardly causing the key 312 to press against the arm 213. When the key 312 is aligned with an annular notch 215, the spring biases the key 312 into the notch 215 and prevents the arm 213 from sliding in the hole 283 relative to the stage 206 as shown in FIG. 10. Pressing the button 284 inwardly compresses the spring 287 and moves the key 312 out of the groove allowing the stage 206 to translate along the arm 213 as shown in FIG. 11.

Figures 12, 13, 14:
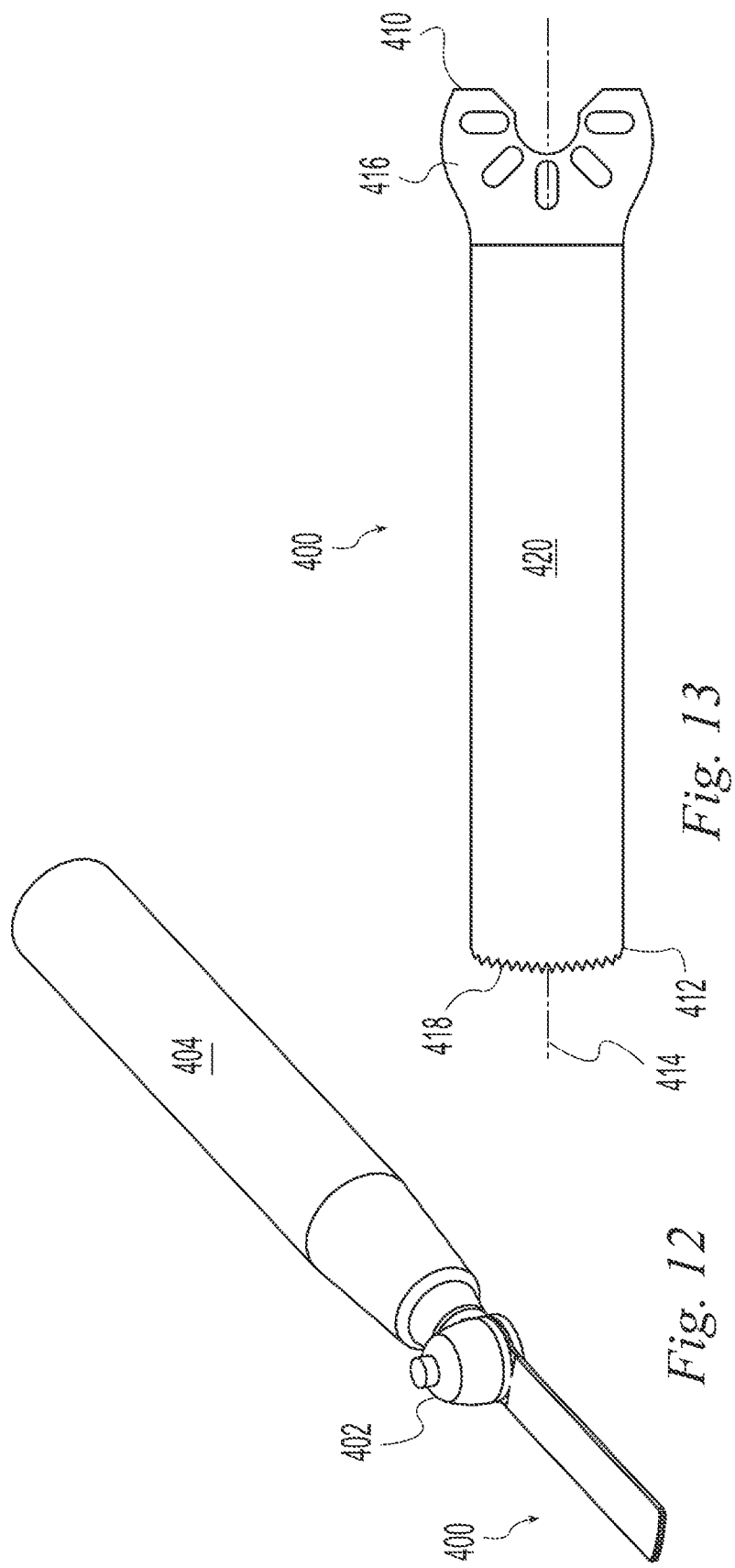
FIG. 12 is perspective view of an illustrative example of a saw blade according to the present invention useable with the guide of FIG. 3 and shown with a powered handpiece.
FIG. 13 is a top plan view of the saw blade of FIG. 12.
FIG. 14 is a side elevation view of the saw blade of FIG. 12.

FIGS. 12-14 illustrate a saw blade 400 useable with the guide 200. The blade may, e.g., be gripped in a chuck 402 of a powered handpiece 404 to drive the blade to cut a bone. In the illustrative example of FIGS. 12-14, the blade 400 is an oscillating blade used with a powered oscillating saw. The blade 400 is a generally plate-like member having a first end 410, a second end 412, and a longitudinal axis 414 extending from the first end 410 to the second end 412. The first end 410 defines a hub 416 adapted for engagement with the powered handpiece 404. The second end 412 defines cutting teeth 418 adapted to cut bone. An intermediate portion 420 having parallel, planar top and bottom surfaces 422, 424 connects the hub 416 and teeth 418. The teeth have a thickness 426 defined perpendicular to the top and bottom surfaces 422, 424. In use, the blade produces a cut having a width, or kerf, equal to the thickness 426. In order for the blade to produce a cut that results in an osteotomy reduction that is in whole units, the thickness 426 is related to the angle of the cut relative to the direction of reduction of the osteotomy which is parallel to the axes 216, 217 of the guide arms. To produce an osteotomy and resulting reduction of one unit length, the thickness 426 is made equal to one unit length times the sine of angle 252. In the illustrative example of FIGS. 3-11, the minimum osteotomy is two millimeters which corresponds to a single cut with the saw blade 400. Therefore, the thickness 426 is equal to two millimeters times the sine of 25 degrees or 0.845 mm. In the illustrative saw blade of FIGS. 12-14, the intermediate portion 420 has a thickness 428 equal to the thickness 426 of the teeth and the saw slot 246 in the inner stage 204 is sized to receive the intermediate portion 420 in close fitting relationship to provide support to the blade 400. In the illustrative embodiment of FIGS. 12-14, the hub 416 has a thickness 430 less than the thickness 428.

Figure 15:
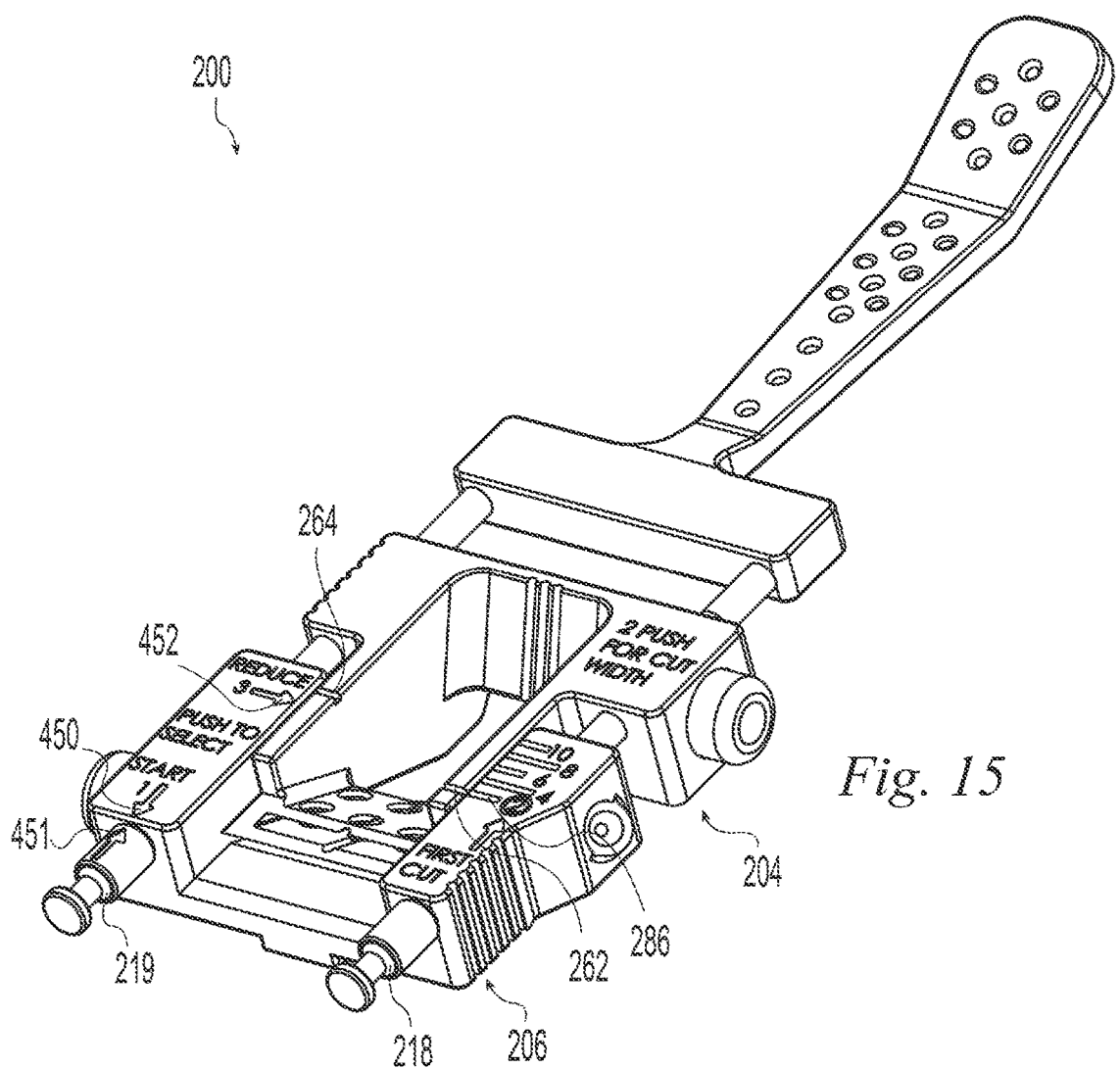
FIG. 15 is a perspective view of the guide of FIG. 3 showing a position of the guide.
Figure 16:
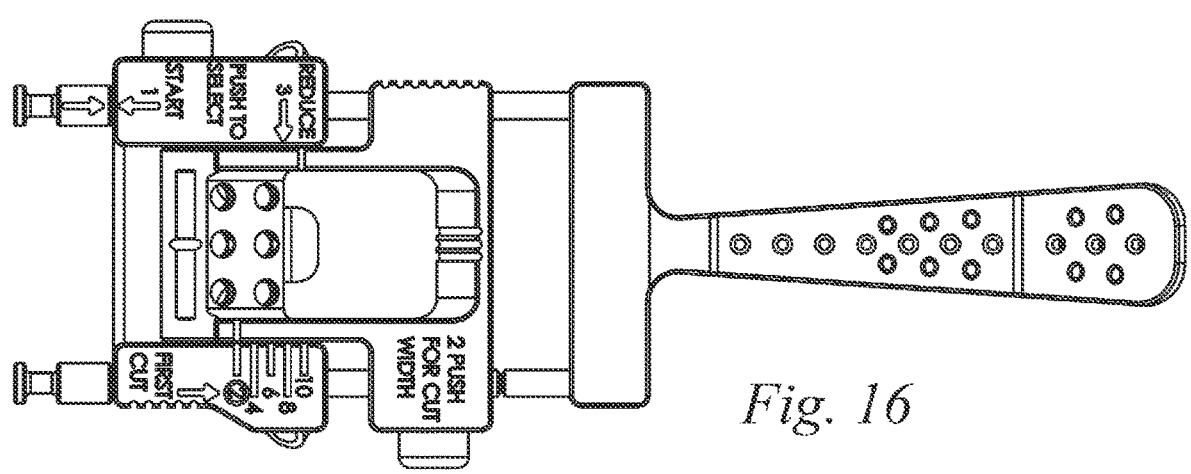
FIG. 16 is a top plan view of the guide of FIG. 3 showing the position of FIG. 15.

FIGS. 15-20 illustrate various positions of the illustrative guide 200 of FIGS. 3-11. FIGS. 15 and 16 illustrate the guide 200 in an initial position in which the outer stage 206 abuts the stops 218, 219 and the inner stage 204 is positioned for a minimal cut. Indicia may be provided to indicate the initial position. In the illustrative example shown, engraved arrows 450, 451 indicate the initial position of the outer stage 206. An arrow 450 on the top surface of the second side 281 of the outer stage 206 points distally at the distal edge of the surface. An arrow 451 on the top of the stop 219 points proximally at the proximal edge of the stop 219. The outer stage 206 is in the first, initial, or start position when the arrows are brought together until the stage 206 abuts the stop 219. The inner stage 204 is in the initial position when the reference mark 262 is aligned with the first of the indicia 286 labeled "2" indicating that a single cut will remove bone resulting in 2 mm of reduction. Note that from this position, the outer stage 206 can be moved 2 mm proximally relative to the inner stage 204 to reduce the osteotomy, or in other words close the gap, created by a single cut with the illustrative saw blade of FIGS. 12-14. This is indicated by an arrow 452 labeled "REDUCE" on the top surface of the outer stage 206 and aligned 2 mm distal of the reference mark 264 on the inner stage 204. In the illustrative example, the stages 204, 206 and annular notches 214, 2154 of the guide arms are arranged to allow positive relative positioning of the stages 204, 206 in 2 mm increments.

Figure 17:
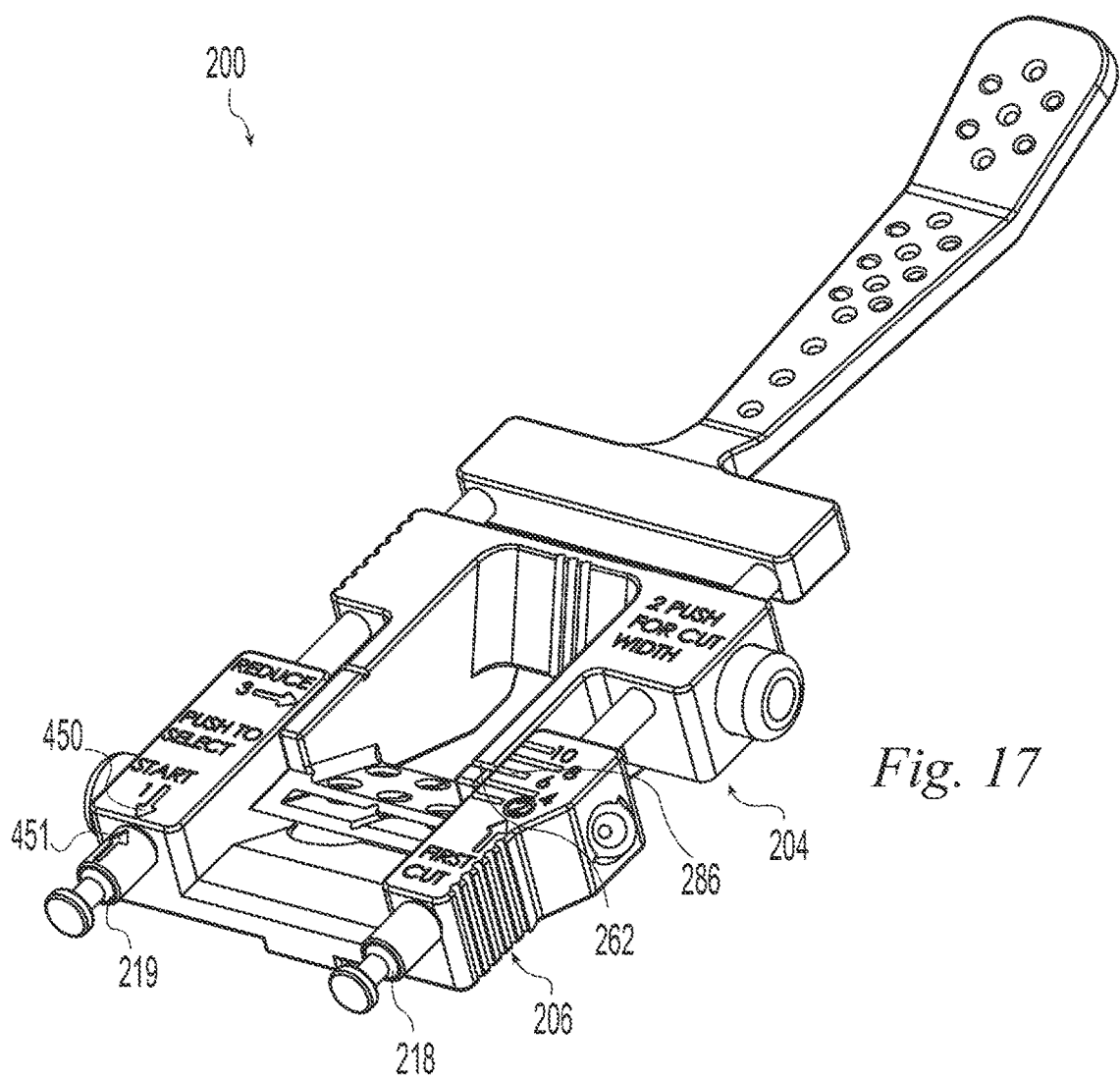
FIG. 17 is a perspective view of the guide of FIG. 3 showing a position of the guide.
Figure 18:
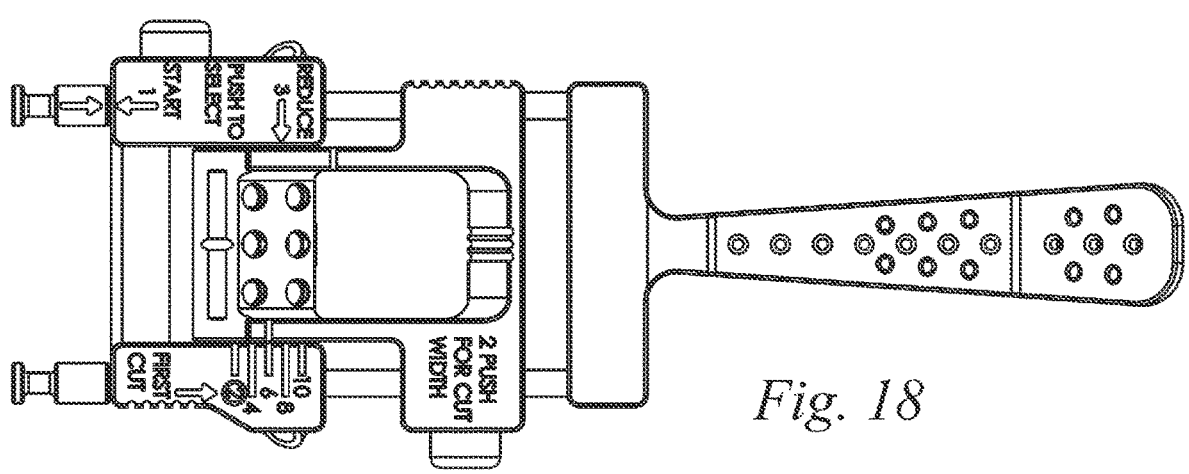
FIG. 18 is a top plan view of the guide of FIG. 3 showing the position of FIG. 17.

FIGS. 17 and 18 illustrate the guide in a second position in which the inner stage 204 has been translated relative to the outer stage 206 and base 202 until the reference mark 262 is aligned with one of the indicia 286 indicating the desired osteotomy reduction if more than 2 mm is desired. In FIGS. 17 and 18, the reference mark 262 is aligned with the indicia labeled "6" indicating that a second cut made with the guide in this position will, in combination with the first cut, remove a section of bone 6 mm long as measured parallel to the guide axes 216, 217 and will thus result in a 6 mm reduction parallel to the guide axes 216, 217.

Figure 19:
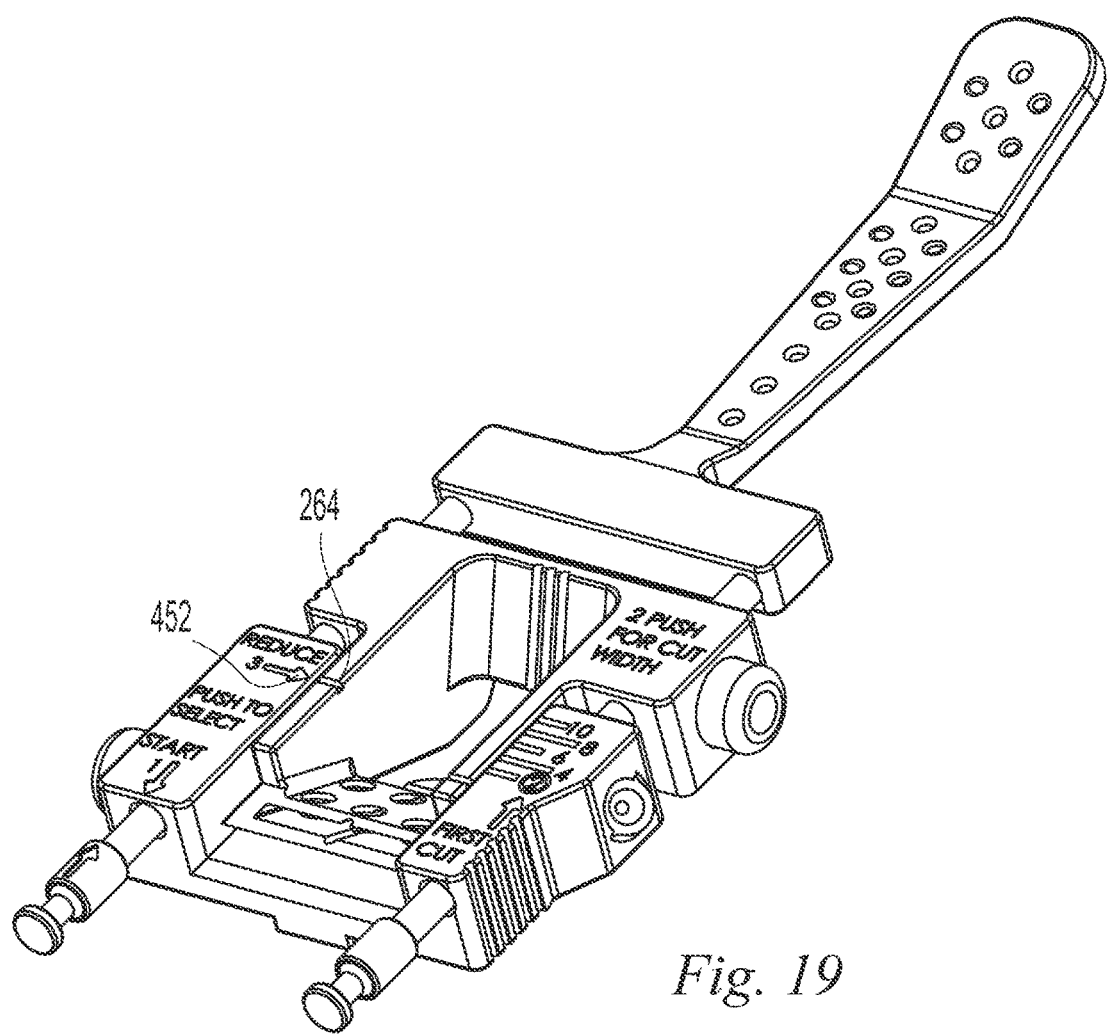
FIG. 19 is a perspective view of the guide of FIG. 3 showing a position of the guide.
Figure 20:
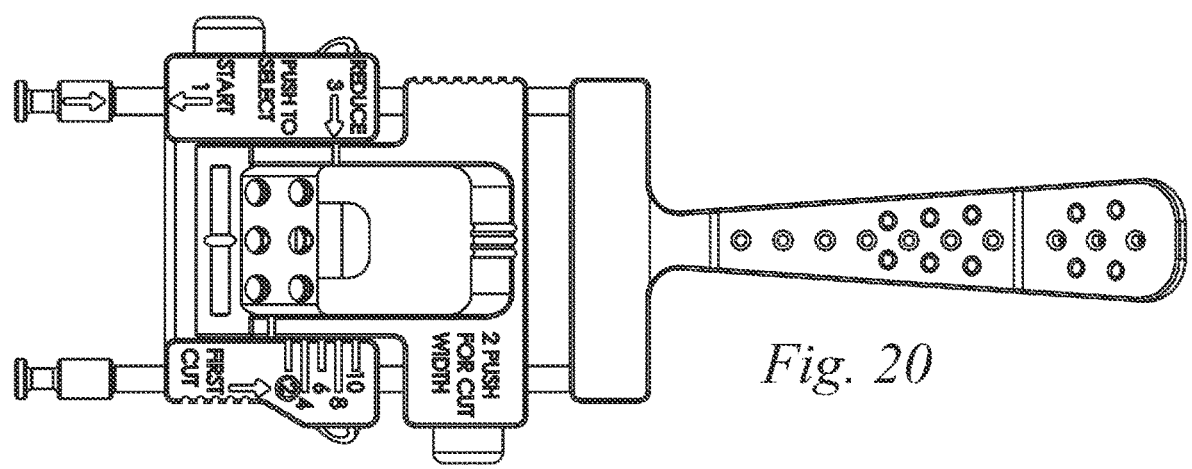
FIG. 20 is a top plan view of the guide of FIG. 3 showing the position of FIG. 19.

FIGS. 19 and 20 illustrate the guide in a third position in which the outer stage 206 has been translated relative to the inner stage 204 and base 202 until the arrow 452 is aligned with the reference mark 264 indicating that the osteotomy has been reduced.

FIGS. 21-31 illustrate the illustrative guide 200 of FIGS. 3-11 in use to form and reduce an osteotomy on a metatarsus 100. In FIGS. 21 and 22, the guide has been placed in the initial position as shown in FIGS. 15 and 16 and placed over the metatarsus 100. The first reference member 220 is inserted into the joint space until the second reference surface 221 abuts the dorsal surface of the metatarsal head 104. The guide is pressed proximally until the reference member 220 abuts the metatarsal head 104. The handle longitudinal axis 209 is aligned with the metatarsal axis 108. The top surfaces of the stages are leveled side-to-side and the cut plane is positioned parallel to the transverse axis. In this position, the guide 200 is registered axially relative to the distal end of the metatarsal head 104 and all six degrees of freedom of the guide 200 have been constrained.

Figure 23:
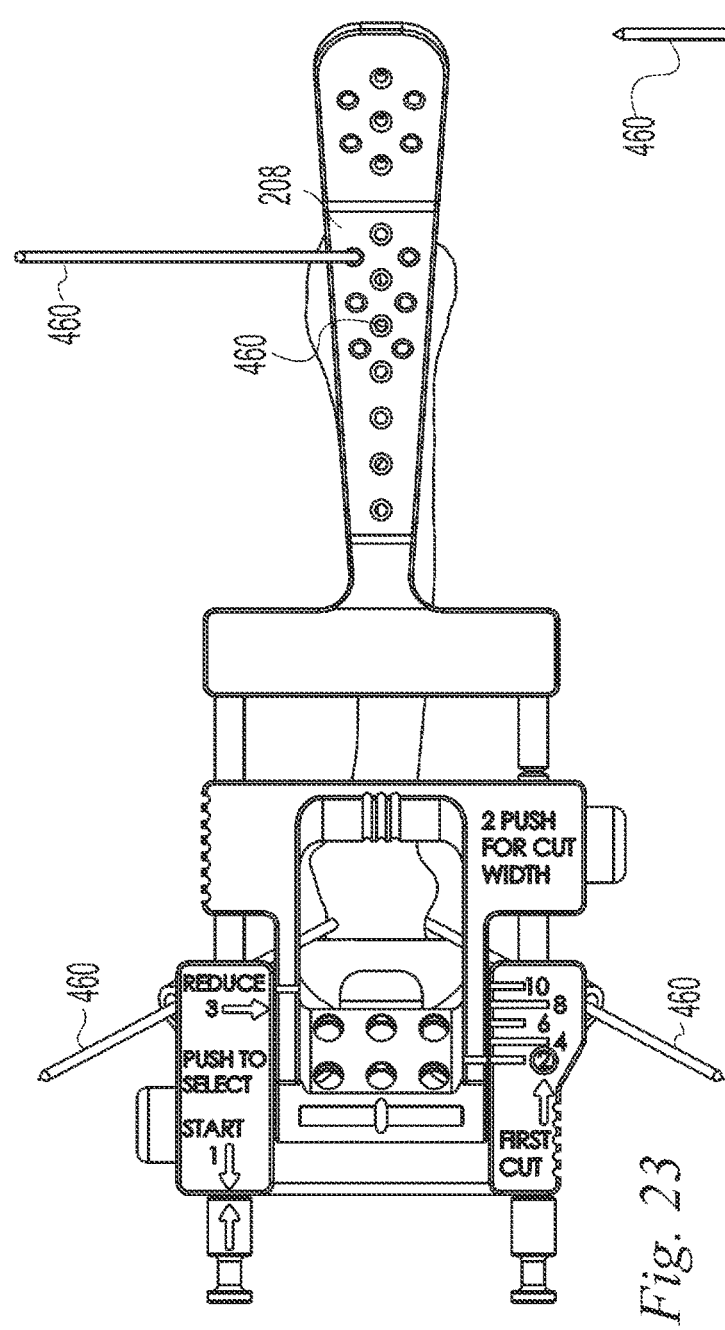
FIG. 23 is a top plan view of the guide of FIG. 3 showing a position of the guide on a metatarsus.
Figure 24:
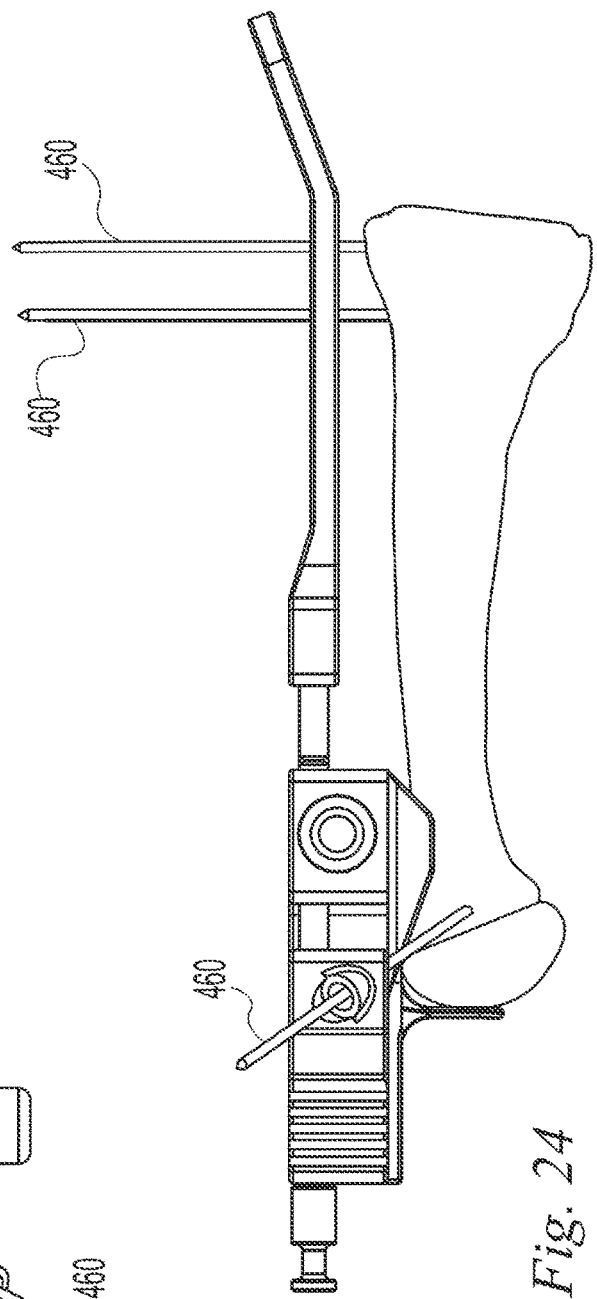
FIG. 24 is a side elevation view of the guide of FIG. 3 showing the position of FIG. 23.
Figure 25:
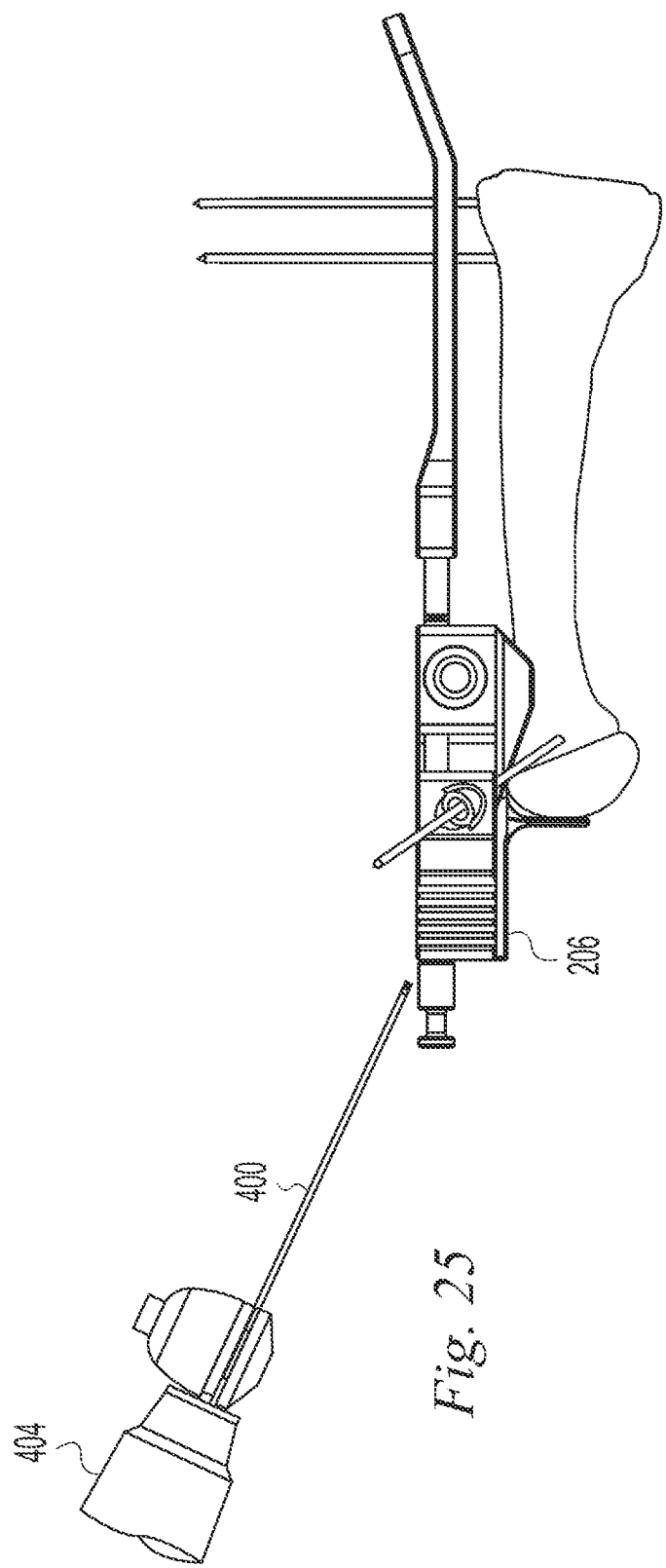
FIG. 25 is a side elevation view of the guide of FIG. 3 showing a position of the guide on a metatarsus ready to receive the saw blade of FIG. 12.
Figure 26:
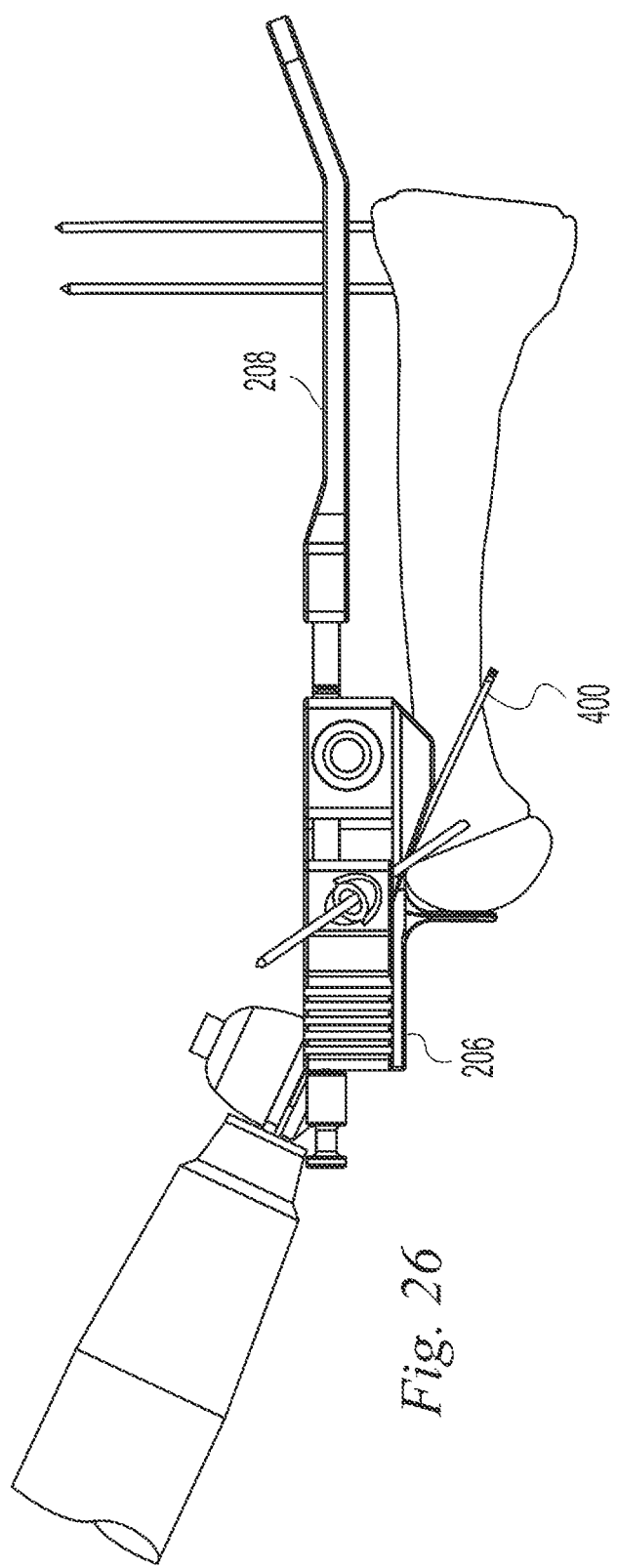
FIG. 26 is a side elevation view of the guide of FIG. 3 showing the position of FIG. 25 with the saw blade advanced to cut the metatarsus.

Referring to FIGS. 23 and 24, the outer stage 206 is affixed to a first portion of the bone, for example at or near the metatarsal head, with fixation members 460, e.g. pins, screws, bands, or the like. The handle 208 is affixed at a second portion of the bone proximal to the first portion.

A cutter is engaged with the cutter guide and advanced to cut the bone. In the illustrative example of FIGS. 25 and 26 a saw blade 400 is engaged with the saw slot 246 and reciprocated via a powered handpiece 404 to separate the metatarsus into a distal portion affixed to the outer stage 206 and a proximal portion affixed to the handle 208.

If more than a 2 mm osteotomy reduction is desired, the inner stage 204 is adjusted to the desired amount of reduction by pressing the button 260 to unlock the stage and sliding it to reposition the cutter guide for a second cut. In the illustrative example of FIGS. 27 and 28, the inner stage 204 is adjusted to remove bone corresponding to a 6 mm osteotomy as indicated by the alignment of the reference mark 262 with the indicia 286 labeled "6".

Figure 29:
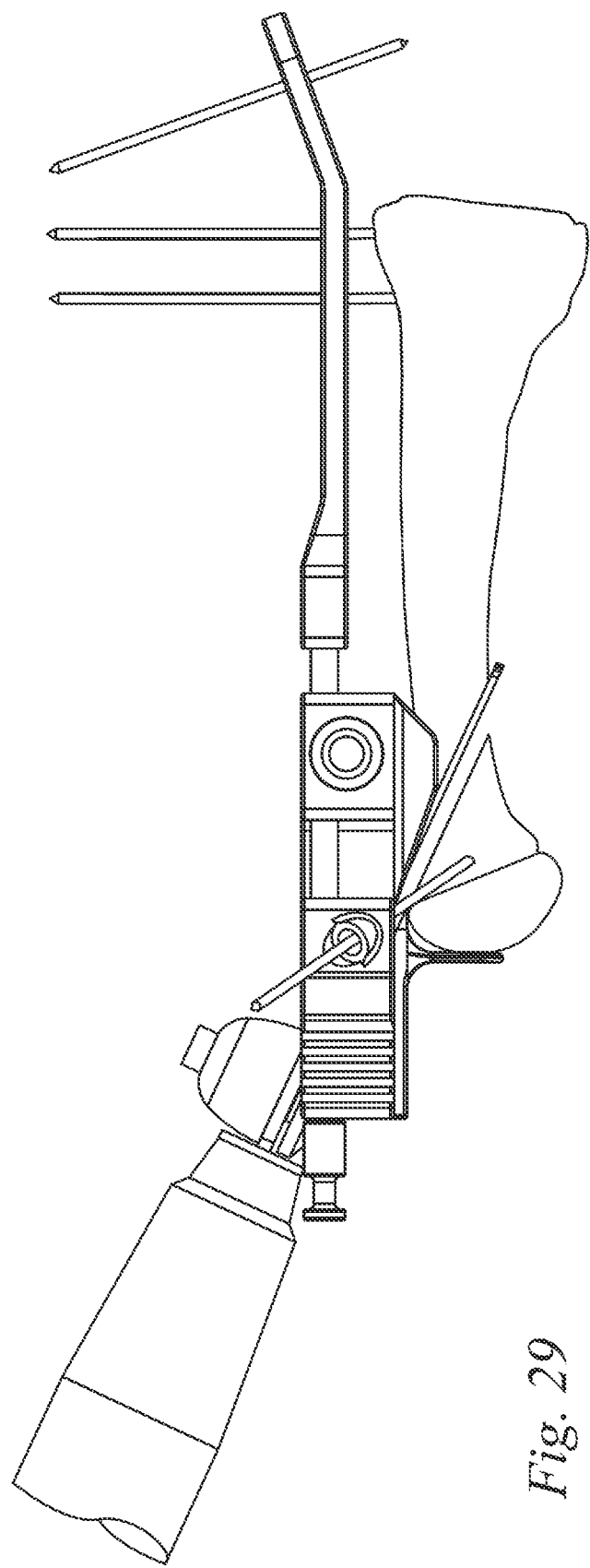
FIG. 29 is a side elevation view of the guide of FIG. 3 showing the position of FIG. 27 with the saw blade advanced to cut the metatarsus.

The saw blade is advanced a second time to cut the bone and any loose pieces of bone are removed to yield the desired osteotomy as shown in FIG. 29.

The osteotomy is reduced by moving the outer stage with the attached metatarsal head until the osteotomy is closed. In the illustrative example of FIGS. 30 and 31, the button 284 is pressed to unlock the outer stage 206 and the outer stage 206 and affixed metatarsal head 110 are translated proximally parallel to the guide axes 216, 217 until the distal portion of bone abuts the proximal portion of bone and the osteotomy is closed. Complete reduction is also indicated by the arrow 452 aligning with the reference mark 264.

One or more fixation devices, e.g. a screw, pin, wire, cable, or the like, may be used to affix the proximal and distal portions of bone. For example pins may be inserted through the metatarsus to join the portions of bone. Pins may be inserted freehand or guided. In the illustrative example of FIGS. 30 and 31, pins 454 are inserted by guiding them in grooves 245 to orient them at a desired angle relative to the osteotomy; for example perpendicular to the osteotomy.

FIG. 32 depicts an illustrative example of a screw assembly 461 useable as an alternative to pins 454 to join the bone portions. The screw assembly 461 includes a screw 462 having a threaded shaft 464 with a distal self-drilling, self-tapping tip 466 and a proximal head 468. A driver 470 is joined to the head 468 of the screw in torque transmitting relationship. In the illustrative embodiment of FIG. 32 the screw 462 and driver 470 are formed as a unitary member with a tapered connecting portion 472 able to transmit torque but able to be broken by bending the assembly at the portion 472.

FIG. 33 depicts an illustrative example of a screw assembly 480 similar to assembly 461 but having three screws 462 stacked to form the assembly. In use, after the distal screw is driven, it is separated from the others by bending at tapered connection 482. Each subsequent screw may be driven and separate in like manner. In this way, three screws may be driven in quick succession without the need to take time to load each individual screw on a driver or change the driver and without risk of dropping a screw.

Figure 34:
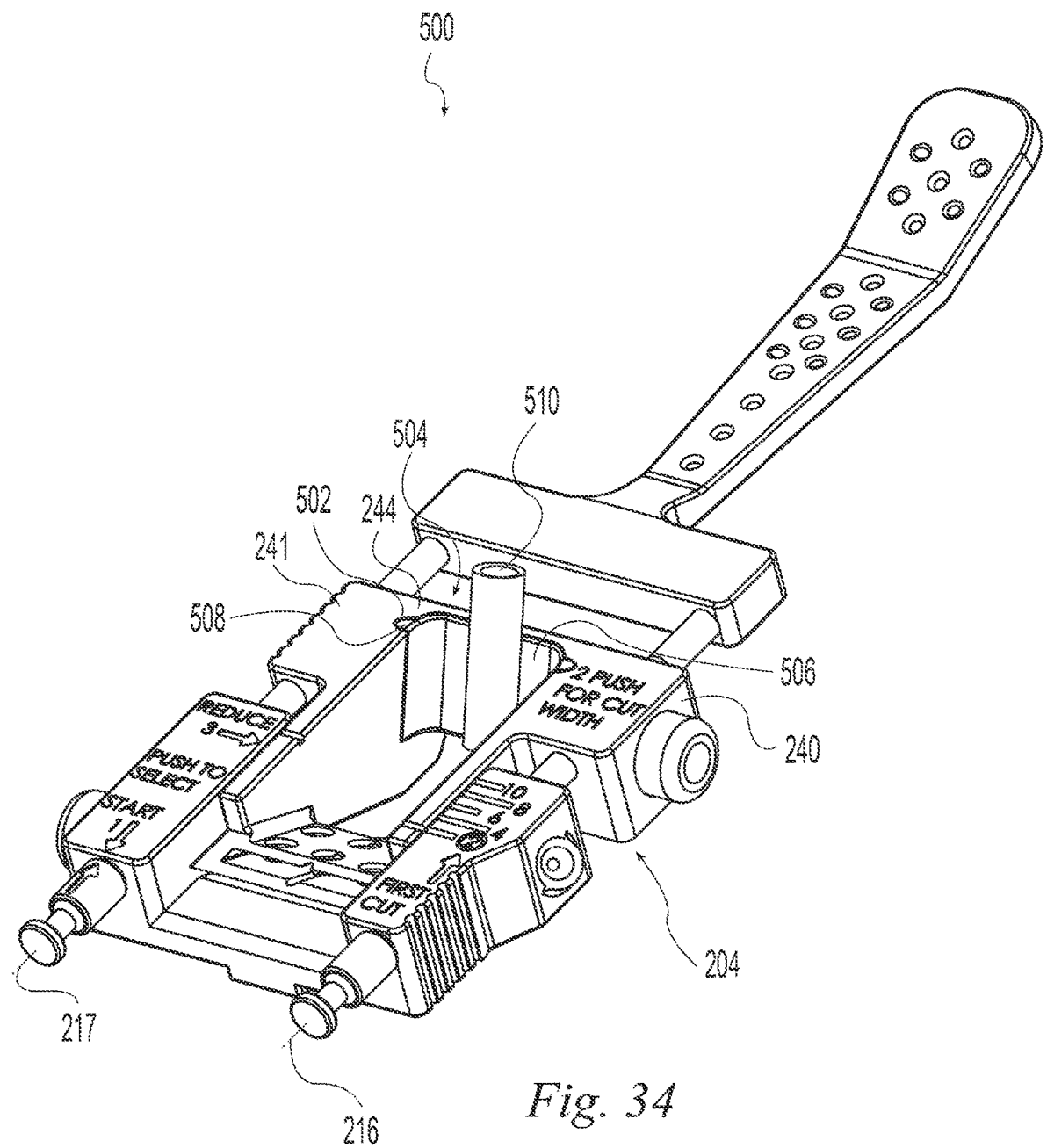
FIG. 34 is a perspective view of an illustrative example of a guide according to the present invention.

FIG. 34 depicts an illustrative example of a guide 500 similar to the illustrative guide 200 of FIGS. 3-11. However, guide 500 includes slots 502 in the sides 240, 241 of the inner stage 204 near the second end wall 244 to receive a modular drill/fastener guide 504 having a frame 506 with outwardly extending tabs 508 engageable with the slots 502. A tubular guide member 510 is mounted on the frame 506. The tabs and slots allow the drill/fastener guide 504 to be engaged with the inner stage 204 in predetermined known relationship to the guide axes 216, 217 and thus the osteotomy when the axes 216, 217 are aligned with the bone axis 108. In use, after the osteotomy is reduced, the drill/fastener guide 504 is mounted on the inner stage 204 and used to guide drills, pins, screws or any other suitable member into the underlying bone in a predetermined orientation. In an alternative example, the drill/fastener guide 504 is permanent part of the guide 500.

The illustrative instruments and methods have been shown in use to create and reduce an osteotomy on a metatarsal bone adjacent the second MTP joint of the human foot. However, guides and methods within the scope of the invention may be used with any bone in the foot, hand, or other part of a patient's body. Likewise, the illustrative instruments and methods have been shown in use to carry out a constrained, axial, linear reduction of the osteotomy. However, other reductions also fall within the scope of the invention. For example, the guide can be configured to move the cut portions of bone linearly at some angle transverse to the bone axis to produce an offset reduction. In another example, the guide can be configured to move the cut portions of bone relatively along a curved path such as for example for reducing a wedge osteotomy. For example, the guide may include hinges, curved tracks, or the like to produce any desired reduction motion.

The illustrative instrument has been shown with a base, inner stage, and outer stage. However, the first and second stages may be mounted for relative motion without the need for a separate base member. For example, the first stage may be connected to a first bone portion and the second stage may be connected to a second bone portion. The first stage may include a cutter guide to guide a cutter to cut the bone. The first stage may include additional cutter guides to guide additional cuts. For example the first stage may include a series of spaced apart saw blade slots to guide a saw blade to remove a desired thickness of bone. The stages may then be moved relative to one another to reduce the osteotomy.

What is claimed is:

1. A method of performing an osteotomy on a bone having a first bone portion and a second bone portion, the method comprising:
    positioning an osteotomy guide near the bone, the osteotomy guide including a first member having a cutting guide and a second member mounted for movement along a predetermined guide motion path relative to the first member;
    attaching the first member to the first bone portion;
    attaching the second member to the second bone portion;
    guiding a cutter with the cutting guide to separate the first and second bone portions into relatively moveable portions;
    moving the second member relative to the first member to move the bone portions relative to one another along a predetermined bone motion path; and
    prior to guiding the cutter, positioning the cutting guide relative to a guide structure using a first reference mark on the cutting guide and aligning the first reference mark with a second reference mark on the guide structure indicating an initial cut position.

2. The method of claim 1 further comprising, after guiding the cutter:
    repositioning the cutting guide relative to the guide structure with the first reference mark on the cutting guide aligning with a reference mark on the guide structure indicating the amount of bone that will be removed with a second bone cut; and
    guiding the cutter with the cutting guide to form a second bone cut.

3. The method of claim 2, wherein the cutting guide and guide structure include reduction indicia, the method further comprising translating the guide structure until the reduction indicia of the cutting guide aligns with reduction indicia of the guide structure.

4. The method of claim 2, wherein the bone is a metatarsal bone of a human foot and the guide structure includes a reference member, the method further comprising, before attaching the first member to the first bone portion, engaging the guide structure with an articular surface of the metatarsal bone.

5. The method of claim 2, wherein the bone is a metacarpal bone of a human hand and the guide structure includes a reference member, the method further comprising, before attaching the first member to the first bone portion, engaging the guide structure with an articular surface of the metacarpal bone.

6. The method of claim 1 further comprising inserting a fixation member to secure the first and second bone portions together.

7. A method of performing an osteotomy on a bone having a first bone portion, a second bone portion, and a longitudinal axis extending from the first bone portion to the second bone portion, and at least one articular surface, the method comprising:
    positioning an osteotomy guide near a bone, the osteotomy guide including a base member defining a base member axis, a cutting guide mounted relative to the base member in linear translating relationship parallel to the base member axis, and a reduction guide mounted relative to the base member in linear translating relationship parallel to the base member axis, wherein the osteotomy guide defines a finite number of discrete positions at which the cutting guide and reduction guide may be selectively located relative to the base member;

attaching the base member to the first bone portion with the base member axis aligned with the bone longitudinal axis;

attaching the reduction guide to the second bone portion;

guiding a cutter with the cutting guide to form a first bone cut to separate the first and second bone portions into relatively moveable bone portions;

translating the reduction guide relative to the base member to move the second bone portion toward the first bone portion parallel to the bone longitudinal axis.

8. The method of claim 7 further comprising: inserting a fixation member to secure the first and second bone portions together.

9. The method of claim 7, wherein the cutting guide includes a cutting slot, and wherein the method further comprises guiding the cutter along the cutting slot to form the first bone cut at a predetermined orientation.

10. The method of claim 7 further comprising, while translating the reduction guide relative to the base member, constraining the first and second bone portions to motion parallel to the base member axis to reduce the length of the bone along the longitudinal axis.

11. The method of claim 7, wherein the cutter comprises a saw blade.

12. A method of performing an osteotomy on a bone having a first bone portion, a second bone portion, and a longitudinal axis extending from the first bone portion to the second bone portion, and at least one articular surface, the method comprising:

positioning an osteotomy guide near a bone, the osteotomy guide including a base member defining a base member axis, a cutting guide mounted relative to the base member in linear translating relationship parallel to the base member axis, and a reduction guide mounted relative to the base member in linear translating relationship parallel to the base member axis;

attaching the base member to the first bone portion with the base member axis aligned with the bone longitudinal axis;

attaching the reduction guide to the second bone portion;

guiding a cutter with the cutting guide to form a first bone cut to separate the first and second bone portions into relatively moveable bone portions;

translating the reduction guide relative to the base member to move the second bone portion toward the first bone portion parallel to the bone longitudinal axis; and prior to guiding a cutter: the cutter, positioning the cutting guide relative to the reduction guide with a reference mark on the cutting guide aligning with a reference mark on the reduction guide indicating an initial cut position.

13. The method of claim 12 further comprising, after guiding the cutter:

repositioning the cutting guide relative to the reduction guide with the reference mark on the cutting guide aligning with a reference mark on the reduction guide indicating the amount of bone that will be removed with a second bone cut;

guiding the cutter with the cutting guide to form a second bone cut.

14. The method of claim 13, wherein the cutting guide and reduction guide include reduction indicia, and the step of translating the reduction member includes translating the reduction member until the reduction indicia of the cutting guide aligns with the reduction indicia of the reduction guide.

15. The method of claim 13, wherein the bone is a metatarsal bone of a human foot and the reduction guide includes a reference member, the method further comprising before attaching the base member: engaging the reference member with the articular surface of the metatarsal bone.

16. The method of claim 13, wherein the bone is a metacarpal bone of a human hand and the reduction guide includes a reference member, the method further comprising before attaching the base member: engaging the reference member with the articular surface of the metacarpal bone.

17. A method of performing an osteotomy on a bone having a first bone portion, a second bone portion, and a longitudinal axis extending from the first bone portion to the second bone portion, and at least one articular surface, the method comprising:

positioning an osteotomy guide near a bone, the osteotomy guide including a base member defining a base member axis, a cutting guide mounted relative to the base member in linear translating relationship parallel to the base member axis, and a reduction guide mounted relative to the base member in linear translating relationship parallel to the base member axis, wherein the cutting guide and the reduction guide include indicia indicating multiple relative blade positions;

attaching the base member to the first bone portion with the base member axis aligned with the bone longitudinal axis;

attaching the reduction guide to the second bone portion;

guiding a cutter with the cutting guide to form a first bone cut to separate the first and second bone portions into relatively moveable bone portions;

translating the reduction guide relative to the base member to move the second bone portion toward the first bone portion parallel to the bone longitudinal axis; and guiding multiple bone cuts with the cutting guide to remove a predetermined width of bone measured relative to the base member axis.

18. A method of performing an osteotomy on a bone having a first bone portion, a second bone portion, and a longitudinal axis extending from the first bone portion to the second bone portion, and at least one articular surface, the method comprising:

positioning an osteotomy guide near a bone, the osteotomy guide including a base member defining a base member axis, a cutting guide mounted relative to the base member in linear translating relationship parallel to the base member axis, and a reduction guide mounted relative to the base member in linear translating relationship parallel to the base member axis, wherein the base member includes a pair of parallel, elongated shafts, and wherein each of the cutting guide and the reduction guide includes a pair of holes receiving the elongated shafts in sliding relationship;

attaching the base member to the first bone portion with the base member axis aligned with the bone longitudinal axis;

attaching the reduction guide to the second bone portion;

guiding a cutter with the cutting guide to form a first bone cut to separate the first and second bone portions into relatively moveable bone portions;

translating the reduction guide relative to the base member to move the second bone portion toward the first bone portion parallel to the bone longitudinal axis.

19. The method of claim 18, wherein the method further comprises nesting the reduction guide and cutting guide such that a portion of the cutting guide overlaps a portion of the reduction guide.

* * * * *